US010568810B2

(12) United States Patent
Lin et al.

(10) Patent No.: US 10,568,810 B2
(45) Date of Patent: Feb. 25, 2020

(54) NEEDLE FILTER APPARATUS

(71) Applicant: Saint-Gobain Performance Plastics Corporation, Solon, OH (US)

(72) Inventors: ZhenWu Lin, Pasadena, CA (US); Kenneth D. Adrian, Manassas, VA (US); Kenneth Renfrew, Huntersville, NC (US); Jacob Andrews, Washington, DC (US)

(73) Assignee: SAINT_GOBAIN PERFORMANCE PLASTICS CORPORATION, Solon, OH (US)

( * ) Notice: Subject to any disclaimer, the term of this patent is extended or adjusted under 35 U.S.C. 154(b) by 184 days.

(21) Appl. No.: 15/830,907

(22) Filed: Dec. 4, 2017

(65) Prior Publication Data

US 2018/0092808 A1    Apr. 5, 2018

Related U.S. Application Data

(62) Division of application No. 13/853,609, filed on Mar. 29, 2013, now Pat. No. 9,833,382.

(Continued)

(51) Int. Cl.
*A61J 1/20* (2006.01)
*A61M 5/165* (2006.01)
(Continued)

(52) U.S. Cl.
CPC ........... *A61J 1/2086* (2015.05); *A61J 1/2048* (2015.05); *A61J 1/2096* (2013.01); *A61M 5/165* (2013.01);
(Continued)

(58) Field of Classification Search
CPC ...... A61J 1/2086; A61J 1/2048; A61J 1/2096; A61M 5/165; A61M 5/38; A61M 5/3202;
(Continued)

(56) References Cited

U.S. PATENT DOCUMENTS 5,147,309 A * 9/1992 Hemmerich .......... A61M 5/002
604/122
9,731,083 B2 * 8/2017 Asano ..................... A61M 5/36

FOREIGN PATENT DOCUMENTS

CN     201 987 980 U      9/2011
DE      43 12 852 A1     10/1993
(Continued)

*Primary Examiner* — Philip R Wiest
(74) *Attorney, Agent, or Firm* — Lorusso & Associates

(57) ABSTRACT

Disclosed is a disposable needle filter apparatus with a universal truncated syringe-receiving neck to enable the filtration of fluids/solutions aspirated into a needle-bearing syringe. The apparatus includes a needle seal stopper and needle stop to create a substantially airtight chamber to facilitate fluid aspiration through an enclosed filter and into the syringe. In an alternative embodiment, the filter apparatus includes an extended syringe-receiving neck configured to receive a specifically sized syringe/needle combination. In a further embodiment, the receiving neck is constructed as a modular unit to allow for interchangeable necks to accommodate different needle and syringe sizes with different cross-sectional diameters. In a yet further embodiment, the neck is constructed with stepped tapered segments of serially larger cross-sectional diameters to accommodate differently sized syringes. In a still further embodiment, the apparatus includes an accessory needle secured to the apparatus inlet.

20 Claims, 20 Drawing Sheets

Related U.S. Application Data

(60) Provisional application No. 61/617,077, filed on Mar. 29, 2012.

(51) Int. Cl.
*A61M 5/38* (2006.01)
*A61M 5/32* (2006.01)
*A61M 39/10* (2006.01)

(52) U.S. Cl.
CPC ............ *A61M 5/3202* (2013.01); *A61M 5/38* (2013.01); *A61M 2039/1077* (2013.01); *A61M 2205/7527* (2013.01); *A61M 2205/7536* (2013.01); *A61M 2205/7545* (2013.01)

(58) Field of Classification Search
CPC .. A61M 2039/1077; A61M 2039/7527; A61M 2039/7536; A61M 2039/7545
See application file for complete search history.

(56) References Cited

FOREIGN PATENT DOCUMENTS

| | | |
|---|---|---|
| EP | 0 007 547 A1 | 2/1980 |
| WO | WO 93/22029 A1 | 11/1993 |

* cited by examiner

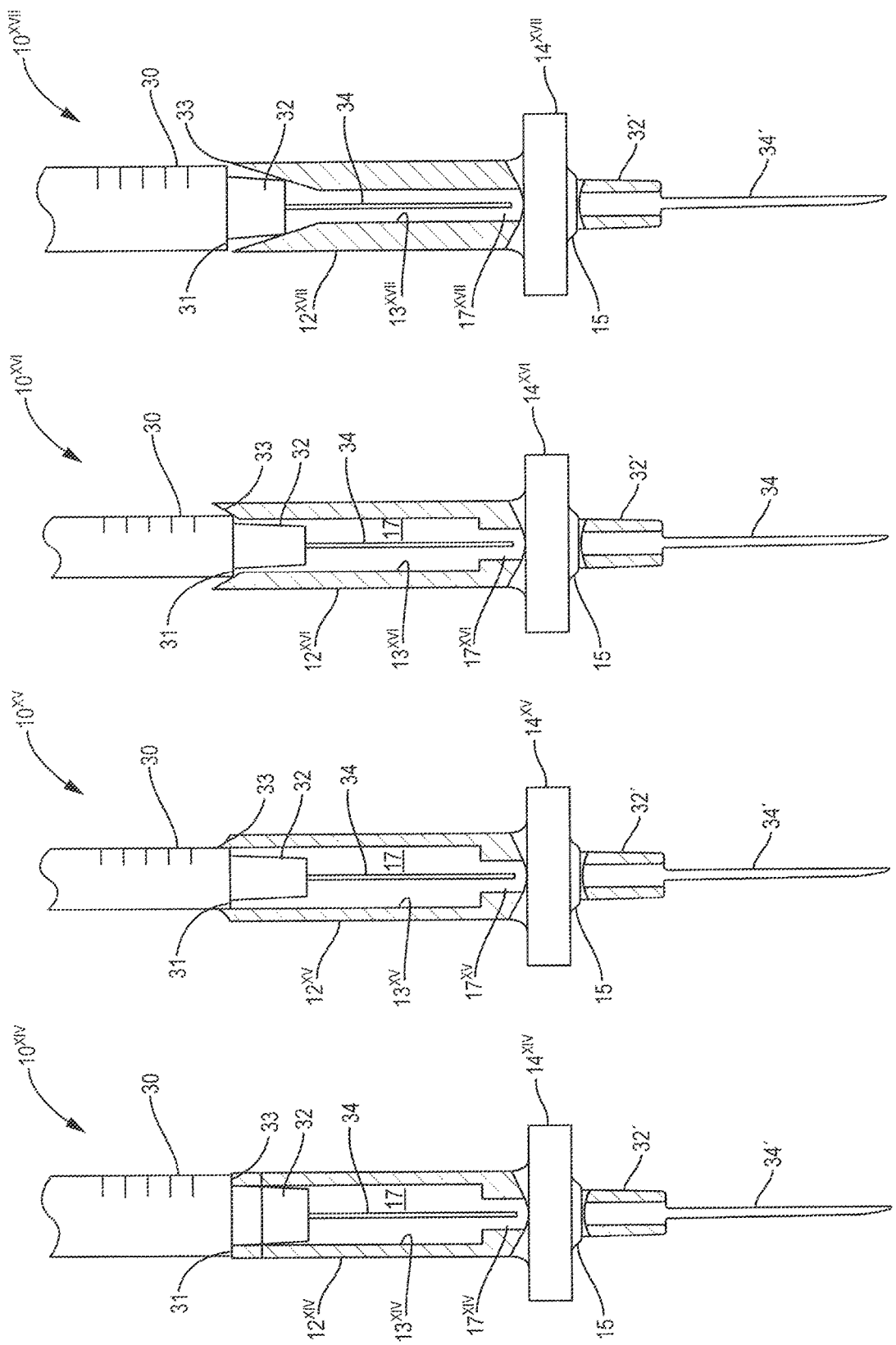

NEEDLE FILTER APPARATUS

CROSS-REFERENCE TO RELATED APPLICATIONS

This is a divisional application of U.S. Regular Utility application Ser. No. 13/853,609, filed on Mar. 29, 2013, now U.S. Pat. No. 9,833,382, Dec. 5, 2017, to which a claim of priority is made and the contents of which are incorporated in their entirety herein by reference. U.S. Regular Utility application Ser. No. 13/853,609 previously claimed the benefit of U.S. Provisional Application Ser. No. 61/617,077, filed Mar. 29, 2012, the contents of which also are incorporated in their entirety herein by reference.

FIELD OF THE DISCLOSURE

The disclosure relates generally to an accessory needle filter apparatus for filtering fluids and solutions aspirated into a syringe or like device. More particularly, the disclosure concerns disposable needle filter apparatus for attachment to syringes bearing needles prior to fluid/solution aspiration into the syringe.

BACKGROUND OF THE DISCLOSURE

A common application of needle-bearing syringes is to draw medicament or drug-laden solutions into the syringes for administration into a human subject via subcutaneous. Intra-muscular and/or intravenous injection. Hypodermic needles and the like are used to perform the tissue penetration and solution administration event. Often times, the solutions are prepared by dissolving a drug in pill, tablet or powder form into an aqueous solvent. The implements used to make the pharmaceutical preparations range from rather sophisticated lab apparatuses in aseptic conditions to more primitive arrangements in which a spoon or like device is used as a mixing vessel with or without the application of heat. In the latter setting, the possibility for solution contamination via environmental factors, e.g., sneezing, coughing, contaminating touching, is considerable.

Apart from the possibility of environmental contamination, the substances used to make the solutions may also pose contamination risks. Although pills and tablets and other powder-based medicaments and medications are designed for relatively safe administration via the alimentary tract, infusion of the same pharmaceutical preparations via hypodermic needle and the like creates a different biological and physiological dynamic in which what is in one setting a safely ingested material becomes a potentially lethal contaminant.

As is well known in the art, drugs in one form or another, but particularly in pill form, are often prepared with waxes, chalky substances, binders, fillers and other additives to ease mechanical ingestion, or to control drug delivery release time, among other functions. Although innocuous substances in the alimentary tract, these same substances can easily be described as undesirable for hypodermic needle injection.

A yet further source of potential solution contamination is the use of needle-bearing syringes for recreational drug use. Apart from the various potential sources of contamination described herein, "needle sharing" adds a significant additional source of potentially lethal contamination. Although biological pathogens may be introduced at any stage of the solution preparation process, transmission of pathogens from one person to another is greatly increased with the use of the same solution with previously used needles.

An even more insidious source of potential contamination can occur in controlled environments, e.g., hospital and clinics, maintained to minimize the presence of pathogens in bacterial and/or viral form. As is commonly known, medications in fluid form including vaccines, often are stored in airtight containers or vials having caps with rubber membranes secured thereto. To obtain a dose of the enclosed medication, a syringe/needle assembly is used to extract the medication. The tip of the needle is pressed against the membrane to pierce it so as to allow entry of the needle. As the needle is advanced, the resilient membrane seals around the needle to prevent air infiltration in one direction and fluid escape in the other.

Although the interior of the container and the medication itself may be sterile, the outside of the container may have surface contamination. For example, the container top may be contaminated by contact transmission of pathogens or via aerial assault, e.g., a health care professional sneezing in close proximity to the container. Microscopic pathogens may be deposited onto the container including the membrane without any visible sign of the contamination. Once the syringe needle is pressed against the membrane for insertion, any contamination on the membrane can be transferred to the outside of the needle and spread along the needle as the needle is advanced through, and retracted from the membrane. Although the contents drawn into the needle and syringe may be sterile and contaminant fee, the outside surface of the needle may harbor contamination obtained from the fluid extraction process.

Unknown to the healthcare professional handling the syringe, use of the same needle to penetrate the skin and tissue of a patient to administer the medication results in exposure of the patient's internal tissues to the contaminant. What is needed is a means to ensure solutions aspired into syringes for subsequent administration are effectively free of environmental and solution-borne contaminants. What is also needed is a means to ensure a needle used for insertion into human tissue to administer medications is free of pathogenic contamination both inside and outside the needle.

Many devices and methods have been developed to address these problems, however, the shortcomings and inefficiencies of these prior attempts are considerable. For example, U.S. Pat. No. 5,125,415 discloses a syringe tip cap. The cap includes an enclosed filter for filtering air from a loaded syringe prior to administration. To use the syringe cap, a desired solution or fluid is drawn into the syringe via an attached hypodermic needle or the like. As is often the case, whatever is drawn into the syringe will include any contaminants in the solution including the aspiration of unwanted air, which, in and of itself, can be considered a contaminant, particularly if the drawn fluid is destined for later intravenous administration, or for lab testing when, for example, blood gas levels are measured if the fluid is drawn blood.

Once the syringe is loaded, the needle is removed and the cap is secured to the syringe. The plunger is then advanced down the syringe barrel while the syringe is held in a substantially vertical orientation with the connection end at the top. This allows lower density gases to migrate to the now top of the syringe where it enters the cap and passes through the enclosed filter. Once the air has been purged, the fluid contacts the filter and causes it to swell so as to seal the cap. This ensures the fluid is maintained in the syringe. The cap is then removed and the fluid is ready for expulsion from the syringe.

The drawbacks of this approach are significant and considerable. First, the cap, by design, does not allow for the flow of fluid through the filter. This prevents the filter from being used to filter any non-gaseous contaminants out of the contained fluid. Second, the cap requires the needle to be removed to perform the filtration step and later re-attached, or replaced with a new needle for further use. This adds considerably to the possibility of a needle stick event, due to the need to handle the needle portion multiple times for one use.

Another approach taken is disclosed in U.S. Pat. No. 3,859,999. In the '999 patent, a single filament is rolled and intertwined into a wad. The wad is placed at the bottom of the syringe barrel or in a bore formed in a needle holder so as to place the wad between the connected fluid channels of the needle holder and the connection end of the syringe. This approach has a similar deficiency to that of the '415 patent in that the needle remains exposed throughout the series of steps taken to load the filter and operate the syringe. The chances for a possible needle stick event are numerous.

U.S. Pat. Appl. Publ. No. US 2008/0097353 discloses a filter secured in a distal end of a syringe needle having frangible sections. Fluid is drawn into the needle and attached syringe through the needle tip. The filter disposed behind the needle tip filters the incoming fluid. Once the fluid has been aspirated to the desired amount, the needle tip including the filter is detached by snapping the needle at the frangible section located behind the filter. The needle tip and filter are thereafter discarded. The section of the needle remaining after the separation has a properly shaped new tip for tissue penetration. Although this approach solves the problem of filtering fluids before entry into the syringe, the constantly exposed needle combined with the manual method used to remove the needle tip presents a constant danger of a needle stick event.

A yet further approach to solve contamination problems with aspirated fluids is shown in U.S. Pat. No. 4,066,079. The '079 patent discloses a filter apparatus that attaches to a syringe at one end, and to needle at the opposing end. The filter apparatus defines a pair of chambers, each having a one-way check valve. One valve is dedicated to permit fluid to flow into the syringe, while the other is dedicated to allow fluid to flow out of the syringe. A filter is lodged behind the outward bound check valve to filter the contained fluid as it flows out of the syringe. Although this system requires less manipulation of the needle, it still presents the problem of an exposed needle with the possibility of a needle prick event. Moreover, part of the chamber through which the fluid is drawn into the filter apparatus contacts the fluid after filtration, but before entry info the hilt of the needle. Any contaminants deposited in the shared chamber can be reintroduced into the fluid as it exits the apparatus into the needle. This counteracts and defeats the purpose of the filter secured in the apparatus to eliminate contaminants before injection of the intended fluid.

A still further approach is disclosed in U.S. Pat. Appl. Publ. No. 2009/0264829 in which a needle sheath with a filter plug secured to a distal end is disclosed. In this apparatus, the sheath encloses the needle and allows for the aspiration of fluid through the filter and into the needle. In one embodiment, the needle tip enters the filter and receives fluid directly through the filter. The tight-fitting sheath allows for the creation of a vacuum in the sheath to promote fluid flow info the needle and syringe. Once the syringe is loaded, the sheath is removed and the syringe is ready for use. Although this approach solves the problem of an exposed needle, it requires the sheath to be fitted to the specific syringe and needle, which can differ considerably with respect to syringe barrel width as well as needle length. Moreover, the design allows for the needle to pierce the filter and has no means to prevent the extent to which the needle pierces the filter.

What is needed and what is provided herein is a universal needle filter assembly that effectively eliminates fluid contaminants from being drawn into a syringe and protects against needle stick events regardless the size and structure of the syringe and/or needle. What is further needed is a disposable needle filter assembly that includes features to completely enclose a syringe needle and a means to create a substantially airtight chamber to allow for the effective aspiration of fluid through the filter and into the syringe in an aseptic, substantially pathogen-free and contaminant-free manner. What is also needed is a needle filter assembly that incorporates a needle stop surface to prevent a syringe needle from penetrating the needle filter when engaged with the needle filter assembly. These and other objects of the disclosure will become apparent from a reading of the following summary and detailed description of the disclosure as well as a review of the appended drawings.

SUMMARY OF THE DISCLOSURE

In one aspect of the disclosure, a needle filter apparatus includes a filter housing in which a filter is secured. Extending from one end of the housing is an integral attachment or inlet port member. Extending from an opposite end is an extended syringe receiving neck configured to receive a combination syringe and needle. A needle stop segment is secured in, or extends integrally from, an inner wall of the receiving neck. A needle sealing stopper is secured in the receiving neck above the stop segment so as to receive the syringe needle.

In another aspect of the disclosure, a needle filter apparatus includes a filter secured in a filter housing. Extending from one end of the housing is an inlet port configured as a barb for connection to tubing and the like, as a slip seal, or as an accessory needle. An opposite end includes an integral truncated syringe receiving neck configured to receive a syringe needle. Extending radially inwardly from an inner wall of the truncated receiving neck is a needle stop segment. Secured above the stop segment is a needle sealing stopper configured to receive a syringe needle. A retention ring, secured within, or integral to, a needle chamber defined by an inner wall of the truncated receiving neck, retains the stopper in the receiving neck.

In a further aspect of the disclosure, a needle filter apparatus includes a modular syringe receiving neck. The receiving neck is configured in multiple dimensioned embodiments to accommodate different sized syringe bodies. In a still further embodiment, an elongate neck is configured with stepped tapered segments of serially larger cross-sectional diameters to accommodate differently sized syringes. These and other aspects of the disclosure will become apparent from a review of the appended drawings and a reading of the following detailed description of the disclosure.

BRIEF DESCRIPTION OF THE DRAWINGS

FIG. 22 is a side sectional view of a needle filter apparatus with an extended neck secured to a syringe/needle assembly according to a still further embodiment of the disclosure.

FIG. 23 is a side sectional view of a needle filter apparatus with an extended neck configured to secure to the barrel of a syringe/needle assembly according to a yet further embodiment of the disclosure.

FIG. 24 is a side sectional view of a needle filter apparatus with an extended neck configured with threading to engage the barrel of a syringe/needle assembly according to an alternative embodiment of the disclosure.

FIG. 25 is a side sectional view of a needle filter apparatus with an extended neck configured with threading to engage a threaded hub of a syringe/needle assembly according to a further alternative embodiment of the disclosure.

DETAILED DESCRIPTION OF THE DISCLOSURE

Figure 1:
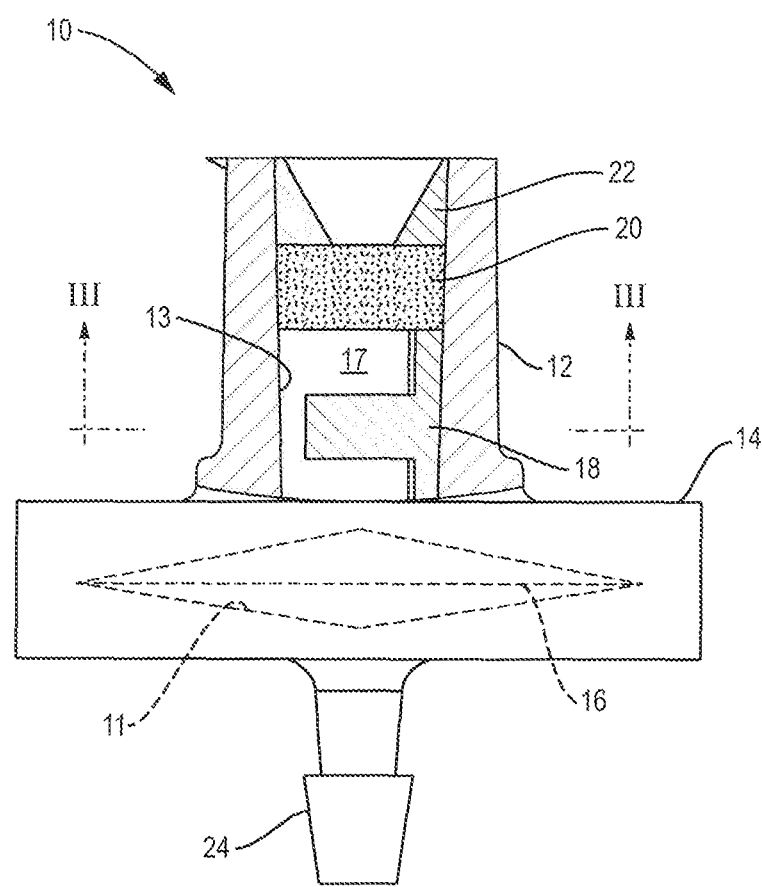
FIG. 1 is a side partial sectional view in partial phantom of a truncated needle filter apparatus according to one embodiment of the disclosure.
Figure 2:
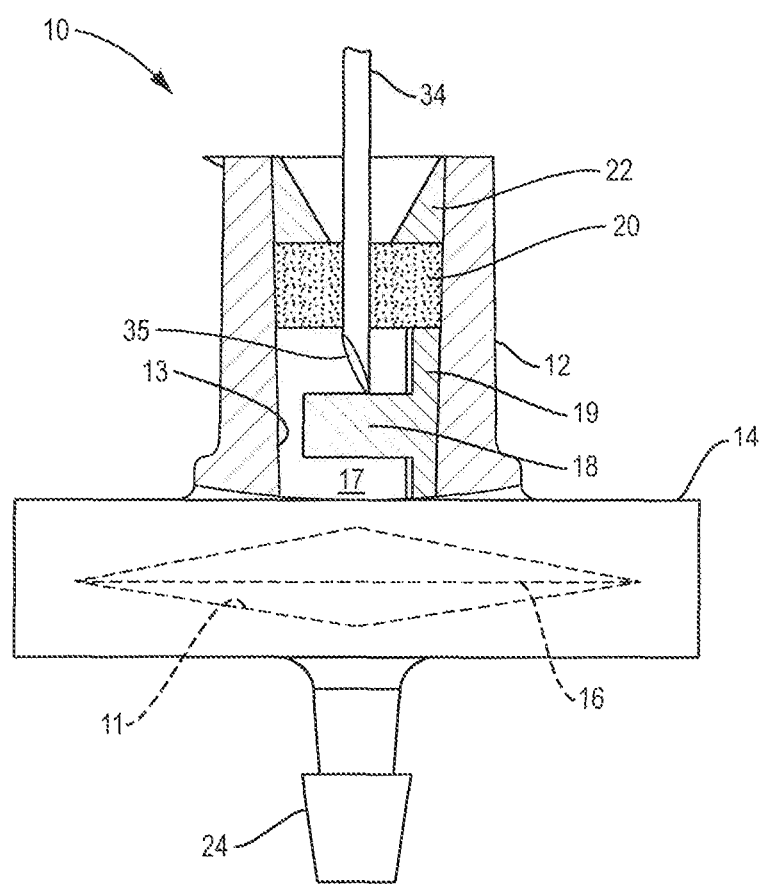
FIG. 2 is a side partial sectional view in partial phantom of the truncated needle filter apparatus shown in FIG. 1 with a needle inserted into the apparatus.

Referring to FIGS. 1 and 2, in one aspect of the disclosure, a truncated needle filter apparatus is shown generally as 10. Apparatus 10 includes a substantially cylindrical body 14 that defines a generally hollow filter chamber 11 configured to hold one or more filters 16. Capsule 10 may be formed in other regular or irregular geometric shapes to accommodate a wide variety of filter configurations secured in the capsule. A primary consideration is to use a filter dimensioned to fill filter chamber 11 sufficient to ensure any fluid that enters body 14 will flow through the filter before exiting.

Extending from a first end of body 14 is hose barb 24 configured to receive tubing and the like. The barb can be used directly as an inlet to receive fluid, or may be used as a connecter to receive an end of a tube, the other end of which is placed into a container from which fluid will be drawn. If barb 24 is used without tubing, apparatus 10 is brought to the fluid source so as to submerge the top of barb 24 in the fluid source for aspiration through apparatus 10 and into a temporarily attached syringe and needle assembly.

Extending from a second end of body 14 is truncated syringe receiving neck 12. Neck 12 is substantially cylindrical in shape and has an inner wall 13 that defines a needle receiving chamber 17 in fluid communication with filter chamber 11. Chamber 17 may be formed in a tapered configuration with the larger diameter end of the taper positioned at an end of neck 12 distal from body 14. Although truncated neck 12 is configured to receive solely the needle of a needle-bearing syringe, the tapered configuration allows for the barrels of differently sized syringes to engage with inner wall 13 so as to set and stabilize the alignment of the needle with a centerline of chamber 17. This is particularly so with respect to relatively short needles in the 6 mm range. The apparatus as structured can accommodate conventional needle lengths of from about 8 mm to about 70 mm, but can also be configured and dimensioned to accommodate needle lengths beyond the recited range.

Figure 3:
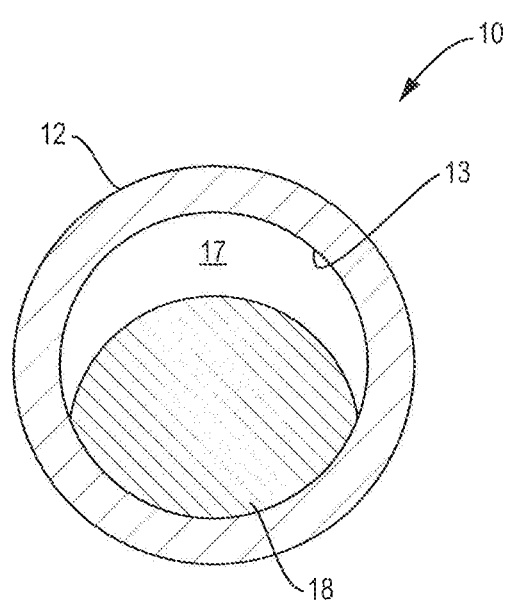
FIG. 3 is a top sectional view of a needle filter syringe receiving neck with a needle stop shoulder according to multiple embodiments of the disclosure.

Referring still to FIGS. 1 and 2 and now FIG. 3, extending radially inwardly from inner wall 13 is needle stop segment 18. Stop segment 18 extends into chamber 17 so as to provide a mechanical barrier to needle travel beyond the shoulder. This ensures any needle inserted into chamber 17, regardless of the angle of insertion, cannot be advanced into body 14 where it could otherwise pierce filter 16 and compromise the filtering function.

In one embodiment as shown in horizontal cross-section in FIG. 3, stop segment 18 has a radiused profile so as to maximize the cross-sectional area available for fluid flow past the shoulder. This allows for the location of the approximate apex of the radius to cross or pass beyond the centerline of chamber 17. It should be understood the radius profile can be altered to conform to any geometric shape including a tortuous irregular "over-under" configuration provided the cross-sectional center point of the plane occupied by shoulder 18 in chamber 17 is physically covered by the shoulder. Although the shoulder could be configured to be shorter, such a configuration will increase the possibility of a needle bypassing the shoulder and entering into the filter chamber.

The radially innermost end of shoulder 18 should be extended at least to the chamber centerline, but can be extended further—by way of illustration and not limitation—to align with an inner rim of a seal retention ring, as more fully described below, so as to further minimize the chance of a needle bypassing the shoulder. The more radially extended shoulder 18 is, however, the less area is available for fluid to pass around shoulder 18. It should be understood the flow path does not have to be large to be effective, but at least should be larger than the inner diameter of the syringe needle. A smaller flow path has the added advantage of reducing the void volume of chamber 17 so as to maximize the fluid recovery from the apparatus. This is particularly relevant and important when the fluid/solution being drawn into the apparatus and the syringe is an expensive drug or medicament.

In integral form, shoulder 18 has portions defining a longitudinal spacer 19 that extends from shoulder 18 in both an upwardly and downwardly direction. A first end extends downwardly from the shoulder and registers against body 14 so as to create a gap between shoulder 18 and the body to allow for fluid to flow from the filter chamber into chamber 17. A second end of spacer 19 extends upwardly and provides a support surface for a stopper 20 more fully described below. This also creates a gap between shoulder 18 and stopper 20 to allow fluid to flow from the filter chamber into chamber 17 and into a needle secured in truncated neck 12.

Figure 12:
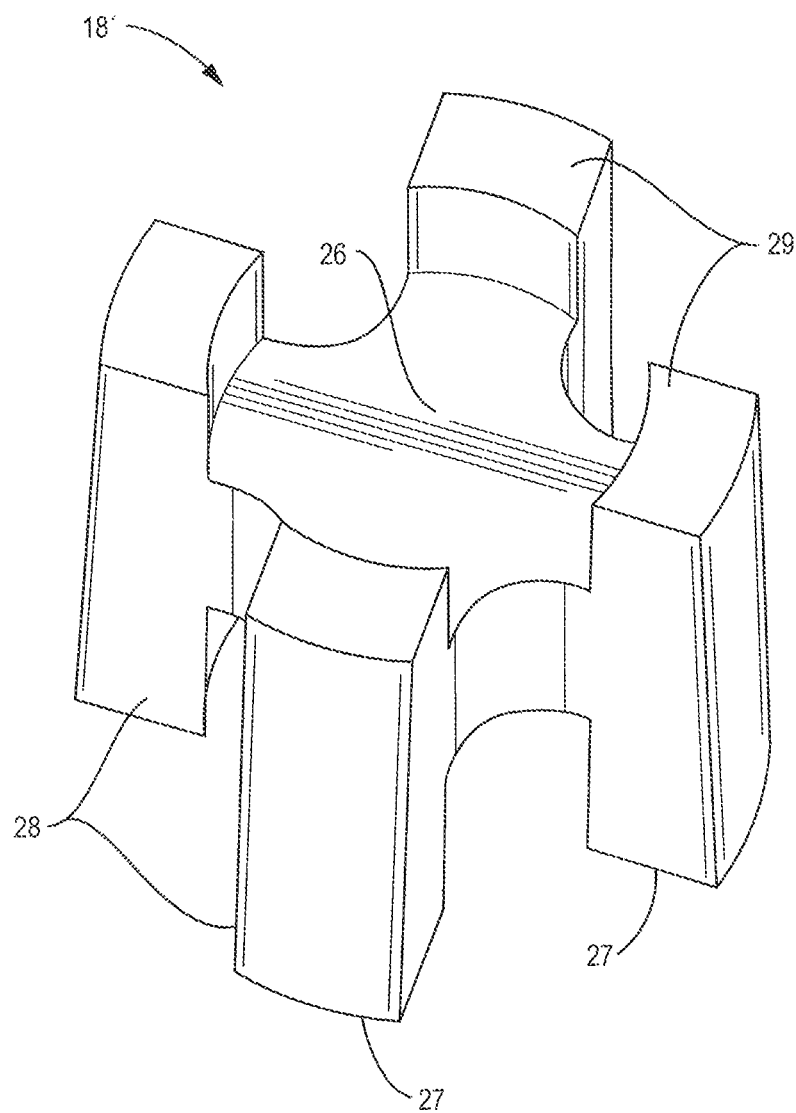
FIG. 12 is a top perspective view of a modular needle stop segment according to one embodiment of the disclosure.

In a modular form as shown illustratively in FIG. 12, stop segment 18 includes a needle strike plate 26 secured between, and continuous with, a plurality of spacer columns 28. Strike plate 26 is substantially planar in configuration to provide a contact surface for a syringe needle. It should be understood, however, that strike plate 28 does not have to have a planar surface to function as a needle stop. This substantially symmetrical construction about a center point is particularly advantageous to prevent needle passage beyond stop segment 18 regardless of the entry point of a syringe/needle assembly at any point about neck 12.

Each spacer column 28 is an elongate structure positioned radially outwardly from, and connected to, strike face 26. Each column 28 has a bottom end 27 configured to register against portions of body 14 so as to form a gap for fluid flow between body 14 and a bottom surface of strike plate 28. Each column 2B also has a top end 29 configured to provide a registration and support surface for stopper 20. The combined top ends 29 provide a stable platform to secure support stopper 20 in neck 12 so as to maintain a gap for fluid flow between strike plate 26 and a bottom surface of stopper 20. Vertical gaps defined between adjacent columns 28 provide fluid passages for fluids/solutions to flow from below strike plate 26 to above the strike plate. A perimeter edge of strike plate 26 formed between the columns may be constructed with inwardly directed radius or scallop profiles to increase the cross-sectional area for fluid flow passed strike plate 28.

Modular stop segment 18 is dimensioned and configured to have outer walls of columns 28 register against inner wall 13 in a friction fit arrangement. Alternatively, modular stop segment 18 may be secured to the inner wall with adhesives, sonic welding, fusion bond, melting the arranged components to fuse them together or via the addition of complimentary structural features to create an interference fit as is well known in the art.

Stopper 20 is a silicone or rubber, substantially disc-shaped element dimensioned and configured for insertion into chamber 17. More specifically, stopper 20 may be constructed from silicon, nitrite, ethylene propylene diene monomer (EPDM), fluoro-elastomers and mixtures thereof. The method of construction may be any conventional method of stopper manufacture well known in the art. There are no special considerations or processes necessary for preparation of stopper 20 for use in apparatus 10 beyond common manufacturing practices.

Stopper 20 is dimensioned to provide a substantially airtight seal when in registration with inner wall 13. The second end of spacer 19 provides a registration surface for stopper 20 that locates the stopper in the proper spatial orientation relative to shoulder 18 when inserted into chamber 17. Stopper 20 functions as a seal when a needle 34 is inserted into the stopper. The material of the stopper collapses around the needle after needle penetration. This, combined with the seal formed at the junction of the stopper and inner wall 13 ensures that chamber 17 is substantially airtight to allow for the creation of vacuum pressure in the chamber when the plunger of an attached needle-bearing syringe is retracted to draw fluid through needle filter apparatus 10 into an open end 35 of a needle 34 from a fluid source.

As is common knowledge to one of ordinary skill in the art, the materials used to make stoppers may have a tendency to adhere to inserted needles so much so that the stopper may migrate out of position when an embedded needle is extracted out of the stopper. To ensure stopper 20 is retained in chamber 17 when needle 34 is extracted from apparatus 10, an annular retainer ring 22 is secured above stopper 20 in registration with a top surface of the stopper. Retainer ring 22 may be integral or modular in design.

If modular, ring 22 may be secured to inner wall 13 via friction fit, interference fit, correspondingly matched threading, adhesive, fusion bonding and the like. If integral, ring 22 may be constructed by melting a top end of neck 12 and forming the retention ring by rolling the melted end into the neck until the melted portion registers against stopper 20. If constructed in an integral manner, the location of a top surface of stopper 20 and retention ring 22 will be more proximate the distal end of neck 12. With an integrally formed ring 22, to achieve the same dimensional gap between a stopper 20 and a stop segment 18 of an apparatus constructed with a modular retention ring, stopper 20 may have to be constructed with a greater thickness (vertical thickness) than one used with a modular retention ring.

An inner wall of ring 22 may have a frustoconical profile in cross section with the narrower diameter end positioned toward stopper 20 and the wider diameter end positioned toward the opening of neck 12. This configuration creates an annular sloping surface that can be used to redirect needles inserted into neck 12 in a non-orthogonal misaligned orientation toward the desirable entry point at the centerline of stopper 20 and chamber 17 so as to ensure registration against shoulder 18 is achieved if the needle is inserted deep enough.

To use apparatus 10, a syringe/needle assembly is lowered into truncated neck 12 with the needle tip in the lead position. The syringe should be lowered into the apparatus in an orientation to align the longitudinal axis of the syringe with a centerline of apparatus 10. It should be understood, however, that the novel configuration, orientation and combination of the truncated neck, sloped retention ring and needle stop permits a user to insert a syringe needle into apparatus 10 at an angle that deviates significantly from the centerline of apparatus 10—including an initial entry point that deviates significantly from the apparatus centerline—so as to stiff achieve needle tip registration against stop segment 18 when the needle is fully inserted into the apparatus. Angular deviations of as much as 45° and greater from the apparatus centerline will result in successful joinder of the syringe/needle assembly to the apparatus.

To continue the insertion process, the syringe/needle assembly is advanced into neck 12 so as to pierce stopper 20 with the needle tip. The syringe/needle assembly is advanced until the needle tip passes completely through the stopper. The assembly may be advanced until the needle tip contacts shoulder 18, but this latter step is not necessary as long as the needle tip has passed beyond stopper 20 into chamber 17. The combined syringe and apparatus is now ready for fluid aspiration.

To aspirate fluid into the syringe, the syringe/apparatus 10 assembly is lowered into a fluid/solution containing vessel or container so as to submerge the end of inlet port 24 below the surface of the fluid/solution. If any accessory elements are attached to port 24, e.g., a tube, the end of the tube is submerged into the fluid/solution. Once this positioning is accomplished, the syringe plunger is retracted so as to create a vacuum in chamber 17. The vacuum is extended into the connected filter chamber and into the inlet port 24 and any attached accessory. This draws the fluid into apparatus 10 through the port, into the filter chamber, through filter 16, into chamber 17, into the needle lumen and into the syringe barrel. Once the desired amount of fluid/solution is drawn into the syringe, apparatus 10 is removed from the syringe needle. Apparatus 10 may be discarded or reused depending upon the aseptic conditions of its prior use.

In one embodiment, filter 16 may be constructed as a hydrophilic porous membrane. As fluid flows into apparatus 10 and onto filter 16, the hydrophilic membrane will be wetted spontaneously and permit the fluid to flow through filter 16 and into the syringe/needle assembly. This construction functions well in normal operation in the absence of air or gas bubbles. When air bubbles enter the apparatus during the fluid aspiration process, the air bubbles will accumulate on the surface of hydrophilic filter 16. This creates an "air-locking" event in which no further fluid can pass through the wetted hydrophilic membrane until the membrane's bubble point pressure is exceeded to clear the air bubble(s) out and allow fluid to flow again. To prevent such air-lock events, a filter 16 constructed with one or more hydrophilic and hydrophobic sections may be used. The differing sections may be co-planar or occupy different planes or levels in the filter so long as fluids/gases introduced into the apparatus will have access to both types of filter sections.

In one advantageous embodiment to prevent "air-lock", filter 16 (in the form of—by way of example—an approximately 13 mm disc membrane) is constructive primarily of a predominantly hydrophilic membrane with a small section (e.g., a 3 mm diameter dot, strip, or even half of the disc membrane) being hydrophobic. As fluid flows into apparatus 10, the hydrophilic section of filter 16 is wetted while the hydrophobic dot, strip, or section remains dry due to its hydrophobicity. Should air and/or gas enter the apparatus, the air and/or gas will pass through the hydrophobic section of filter 16 so as to prevent an air-lock event in the apparatus. The same filter construction can also function to prevent liquid or "water-locking" events when used to filter gaseous fluid that may contain some water. The presence of the hydrophobic and hydrophilic sections on filter 16 permits both gas/air and liquid/water passage and prevent gas/air or liquid/water-locking events (depending upon the application).

Figure 11:
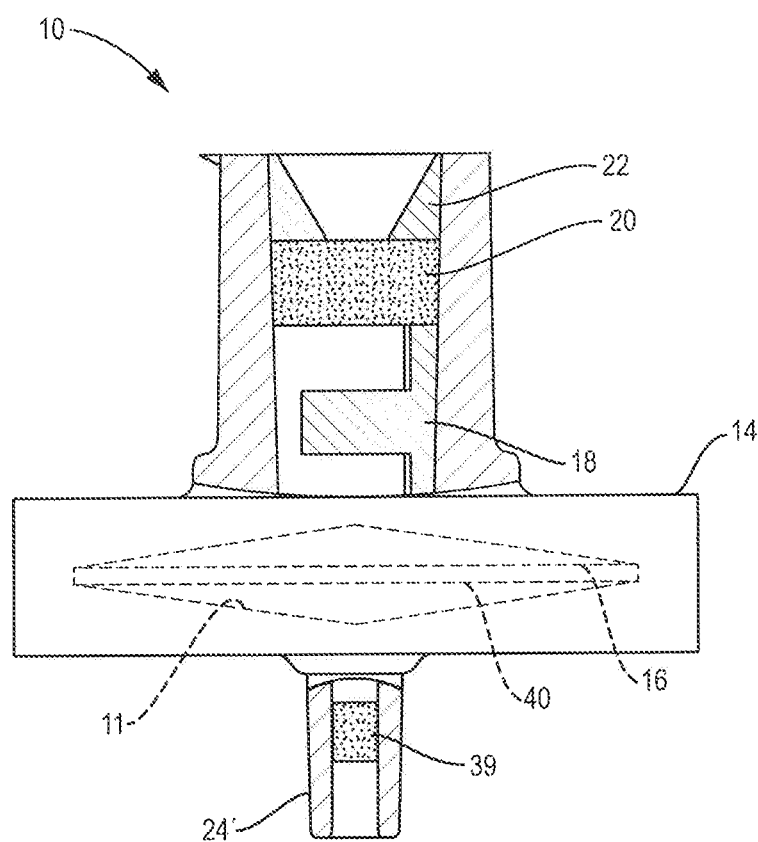
FIG. 11 is a side partial sectional view in partial phantom of a needle filter apparatus with a pre-filter according to a yet further embodiment of the disclosure.

Referring now to FIG. 11, apparatus 10 is shown with an optional ore-filter 39 secured via ultrasonic welding or similar attachment means in an inlet port 24' configured in a slip seal configuration. It should be understood the implementation of a pre-filter is not dictated by the inlet port configuration. Other configurations, barb and luer lock configurations as illustrative examples, can be used in connection with a pre-filter. Pre-filter 39 is included to perform gross filtration of relatively large particulate matter on the order of about 30 μm to about 200 μm in diameter. The mechanisms used to remove relatively large diameter contaminant particles may include non-sieving adsorption, sieving, combination sieving and non-sieving adsorption and the like.

The incorporation of pre-filter 39 (and/or an optional second pre-filter 40 disclosed herein) is used to protect filter 16 from premature plugging by excessive amounts of contaminants that might be in the fluid ultimately drawn through filter 16. Pre-filter 39 and 40 can be used in combination or alone as disclosed more fully herein. As stated, pre-filter 39 is for very course filtration of particles on the order of about 30-200 microns, whereas pre-filter 40 (in a microporous membrane form) may filter particles on the order of from about 0.2 microns to about 3 microns. This is in contrast to filter 16 that may filter particles on the order of from about 0.01 microns to about 1.2 microns. The difference is particle size filtration is dictated by the respective differences in the membrane pore sizes wherein pre-filter 40 has larger pore sizes than filter 16 as disclosed herein.

Pre-filter 39 may be secured in the apparatus at any point upstream of the main filter 16 including an upstream section of filter chamber 11. Alternatively, or in addition, a pre-filter may also be positioned downstream of filter 16 to perform gross filtration for bi-directional flow configurations. As used herein, "upstream" shall mean the side of main filter 16 opposite the side in which a syringe/needle assembly is inserted. Location in inlet port 24' is particularly advantageous to prevent large particulate contaminants from travelling beyond the inlet into the apparatus.

Pre-filter 39 may be constructed from coarse sponge material with pore sizes from about 10 microns to about 200 microns, screen materials such as nylon, polyester with mesh openings from about 20 microns to about 200 microns, or any fibrous filter media formed with micro-glass fibers, nonwoven polymeric microfibers or nanofibers. This ensures only the largest pieces of contaminant matter will be restricted by pre-filter 39. Depth media constructed from polypropylene is another alternative that may be used advantageously for this purpose. Although a hydrophobic polymer, filter material made from polypropylene allows for the passage of air and liquid due to sis low bubble point.

The pre-filter may also be arranged in series with one filter membrane layer registered against one or more additional layers in an orientation substantially perpendicular to the direction of fluid flow through the apparatus. The layers collectively may be hydrophilic, hydrophobic, or a mixture of both. Each layer may be uniformly hydrophilic or hydrophobic, or may include areas modified to have the opposite characteristic. However configured, to ensure air and gas passage through the filter assembly, the hydrophobic section has to be continuous from an upstream surface to a downstream surface of the filter assembly. If hydrophilic layers with modified hydrophobic sections are stacked in series, the hydrophobic sections have to align sufficiently to provide a continuous hydrophobic channel from an upstream to a downstream side of the membrane assembly.

A further optional second pre-filter 40 may be secured (via ultrasonic welding) further downstream from pre-filter 39 in inlet port 24' or in filter chamber 11 upstream of filter 16 so as to provide additional pre-filtration. Alternatively, or in addition, a second pre-filter can be secured in the apparatus downstream of filter 16 for bi-directional flow applications. The construction of pre-filter 40 may conform to any of the variants described for filter 16. The primary difference between pre-filter 39 and second pre-filter 40 (apart from the microporous construction of the pre-filter 40 membrane) is the location of the filters and the retention function in the filtration process.

Pore sizes of each layer of a multilayer membrane assembly, e.g., second pre-filter 40 positioned on the upstream side of filter 16, may be the same for all the layers, or may differ from one layer to another. For membranes used as pre-filter 40, the pore sizes may range from about 0.2 micron to about 10 microns, while filter 16 may have pore sizes from about 0.01 micron to about 5 micron. In one advantageous embodiment, the pore sizes of pre-filter 40 are set to be larger than the pore sizes of filter 16.

When both pre-filter 40 and filter 16 are constructed as hydrophilic membranes, air-locking events can occur. To prevent this, hydrophobic layers or sections may be introduced into the construction. The layers collectively may be hydrophilic, hydrophobic, or a mixture of both. Each layer may be uniformly hydrophilic or hydrophobic, or may include areas modified to have the opposite characteristic. However configured, to ensure air and gas passage through the filter assembly, the hydrophobic section has to be continuous from an upstream surface to a downstream surface of the filter assembly. If hydrophilic layers with modified hydrophobic sections are stacked in series, the hydrophobic sections have to align sufficiently to provide a continuous hydrophobic channel from an upstream to a downstream side of the membrane assembly.

Figure 19:
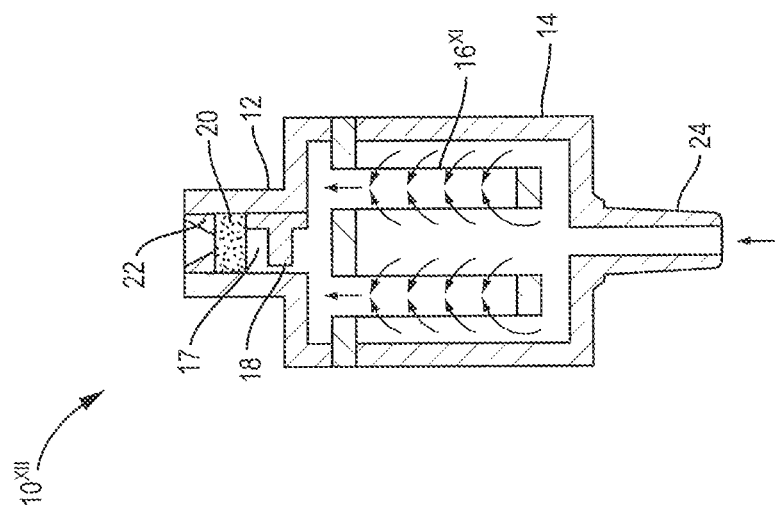
FIG. 19 is a side sectional view of a needle filter apparatus with a hollow fiber membrane in a "U" configuration according to another embodiment of the disclosure.
Figure 20:
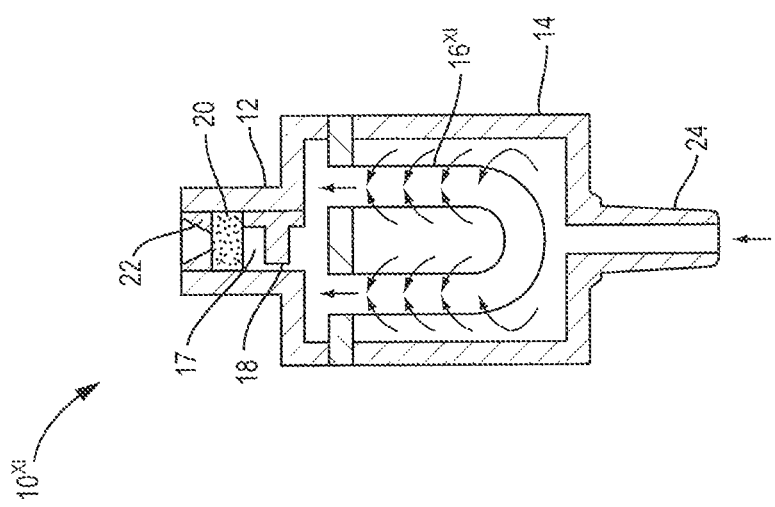
FIG. 20 is a side sectional view of a needle filter apparatus with a hollow fiber membrane according to yet another embodiment of the disclosure.

In this embodiment, filter 16 is positioned downstream from one or more pre-filters to perform the final filtration step in which the smallest sized contaminant particles are removed from the aspired fluid/solution. Like the other disclosed filters, filter 16 may be structured from a single layer or multiple membrane layers. The layers may be configured as "flat" sheets, as tubular or hollow fiber membranes, (annular "U" shaped membrane 16$^{XI}$ in FIG. 19, annular shaped membrane 16$^{XII}$ in FIG. 20 with annular filter end cap 16a), or as combinations of the two configurations. In similar manner to the optional pre-filters, to prevent the possibility of gas lock, hydrophobic layers or hydrophilic layers with modified hydrophobic sections are used to ensure air and gas passage through the filter so as not to inhibit fluid/solution flow through the filter.

Although filter 16 can be constructed with the same materials and configurations disclosed for pre-filter 39, filter 16 differs from any pre-filter present in the apparatus with respect to pore size. Filter 16 is constructed with pore sizes ranging from about 0.01 μm to about 5 μm. Specific pore sizes of 0.1 μm, 0.2 μm, 0.45 μm, 0.8 μm and 1.2 μm are suitable for filter 16. Like the disclosed pre-filters, it should be equally understood with respect to filter 16 that any filter media or membrane configurations disclosed herein may be configured to permit bi-directional flow.

Figure 4:
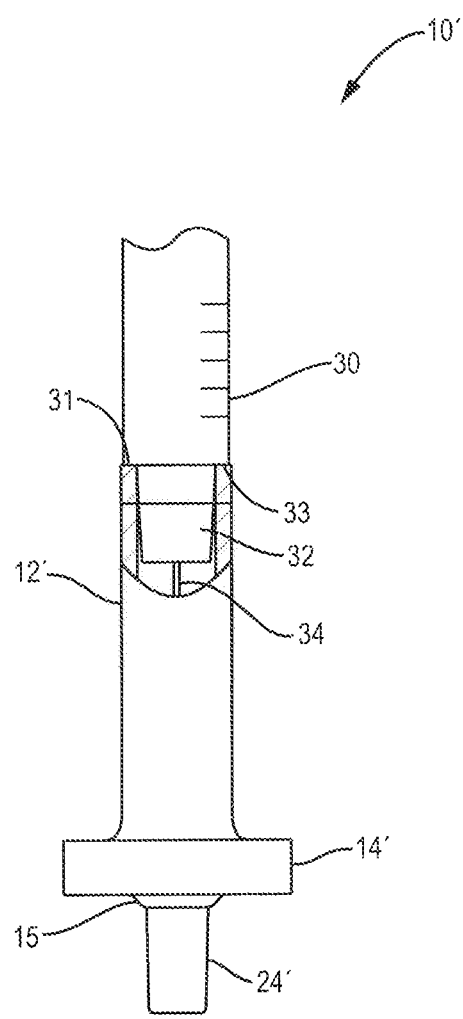
FIG. 4 is a side partial sectional view of a combination needle filter apparatus and syringe assembly according to another embodiment of the disclosure.
Figure 5:
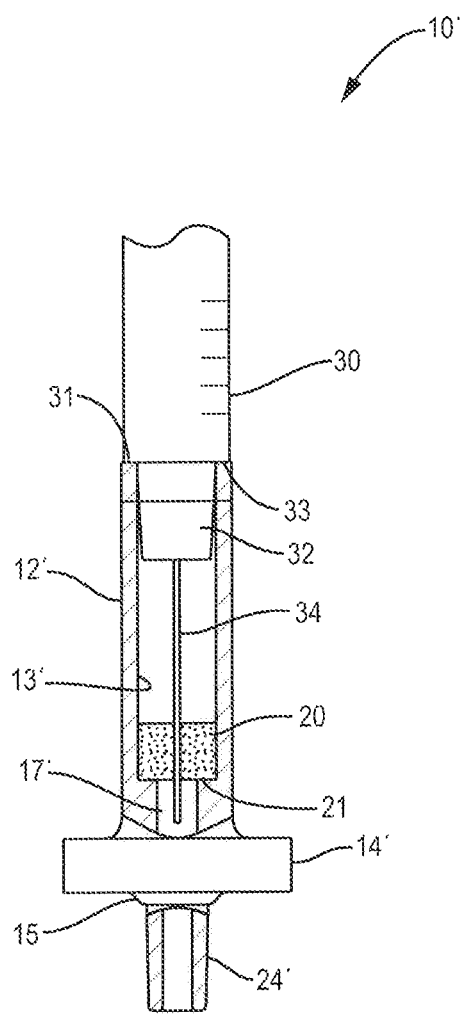
FIG. 5 is a further side partial sectional view of a combination needle filter apparatus and syringe assembly according to the embodiment shown in FIG. 4.

Referring now to FIGS. 4 and 5, in another aspect of the disclosure, a needle filter apparatus shown generally as 10' includes an extended neck segment to engage the distal port and/or barrel of a syringe/needle assembly secured to the apparatus. It should be understood that elements referenced with primed numbers in one embodiment correspond to elements in other embodiments referenced with the same unprimed or differently primed numbers. This embodiment uses additional contact points to improve needle/apparatus alignment and stability, and to prevent needle penetration of the filter membrane.

The primary components of needle filter apparatus 10 shown in FIGS. 1 and 2 are substantially the same for apparatus 10'. Apparatus 10' has a main body 14' that defines a filter chamber for receiving a filter 16'. An inlet port 24' in the form of a slip seal (shown), barb (shown in FIGS. 1 and 2), luer lock and the like extends from a first end of body 14' has portions defining a port chamber in fluid communication with the filter chamber. Inlet port 24' may also include an annular ring 15 to improve structural support at the junction of the inlet to body 14'.

Extending from a second end of body 14' is extended syringe receiving neck 12'. Neck 12' is substantially cylindrical in shape and includes an inner wall 13' that defines a cylindrically shaped needle chamber 17'. Chamber 17 may be tapered in longitudinal cross-sectional shape with the larger diameter end of the taper positioned at the end of neck 12' distal from body 14'. The tapered configuration allows for the neck's distal end to receive distal ports 32 and/or barrels of syringes 30 of various cross-sectional diameters. Larger diameter syringes inserted into the distal end of chamber 17' slide less of a distance into the chamber until an outer wall of the syringe distal port 32 and/or barrel wall engages inner wall 13' in a friction fit connection. Conversely, syringes with smaller cross-sectional diameter barrels can be inserted further into chamber 17' before registering against and forming a seal with inner wall 13'. This creates a substantially airtight seal at the plane occupied by the leading segment of the syringe that engages inner wall 13'.

Although this embodiment requires the cross-sectional dimension of neck 12' to be customized for differently sized syringes, the extra contact between the syringe barrel and the extended neck provides additional support to secure the needle in the apparatus. The registration of the syringe barrel against inner wall 13' improves and ensures the attached needle is substantially aligned with the centerline of stopper 20' substantially orthogonal to the plane occupied by stopper 20' so as to positively engage shoulder 18' after penetration of stopper 20'. This significantly reduces the possibility of bypassing shoulder 18'.

The registered surfaces of the neck and syringe port may form a slip seal, friction fit connection, or may be constructed with other elements to create interference fit or luer lock type connections. It is within the spirit and scope of the disclosure to use any conventional method of securing a syringe body to neck 12'.

Portions of a region of inner wall 13' proximal to, but separate from body 14' define an annular stopper support shoulder 21 configured and dimensioned to provide a registration surface for stopper 20. Stopper 20 is inserted into the open end of neck 12' and advanced info the neck until in contact with shoulder 21. The placement of shoulder 21 on inner wall 13' can be varied to enlarge or reduce chamber 17'. As should be understood by anyone of ordinary skill in the art, a smaller chamber 17', by volume, reduces the overall distance aspired fluid has to travel in order to enter into needle 34.

Stopper 20 is dimensioned to expand into inner wall 13' to form a substantially airtight seal. A stopper retainer ring 22 may or may not be inserted above stopper 20 to secure the stopper in its position when needle 34 is retracted from the assembly. If ring 22 is incorporated into neck 12', it does not require the sloped inner annular surface as extended neck 12' assists and performs the syringe/needle alignment to apparatus 10'.

In this embodiment, a needle stop shoulder is not required to limit the travel of needle 34 in neck 12'. In place thereof, a fop annular surface 31 of neck 12' functions as a stop by engaging an annular syringe shoulder 33 formed by the junction of the syringe barrel and syringe port 32. In an alternative embodiment, a needle stop shoulder can be incorporated into neck 12' positioned between body 14' and stopper shoulder 21. The same criteria and conditions necessary for the construction of shoulder 18 in the truncated neck version apply equally to a corresponding shoulder in extended neck 12'.

To use this embodiment, a needle-bearing syringe 30 is inserted into neck 12' until syringe shoulder 33 registers against neck surface 31. In the process of towering syringe 30 into neck 12', needle 34 should pierce stopper 20 completely through so that needle tip 35 (shown in FIG. 2) is resident in chamber 17'. This ensures the lumen of needle 34 is in fluid communication with chamber 17', which, in turn, is in fluid communication with the filter chamber and the fluid channel of inlet port 24'. If needle 34 does not completely penetrate stopper 20 before syringe 30 engages neck shoulder 31, the proper orientation will not be achieved to generate a vacuum in chamber 17' to draw fluid into the apparatus and syringe when the syringe plunger is retracted. Accordingly, the version of apparatus 10' chosen for a specific syringe/needle assembly must be selected not only on the basis of the neck cross-sectional diameter, but also by its length to ensure full penetration of stopper 20 when the syringe is engaged to apparatus 10'.

Figure 6:
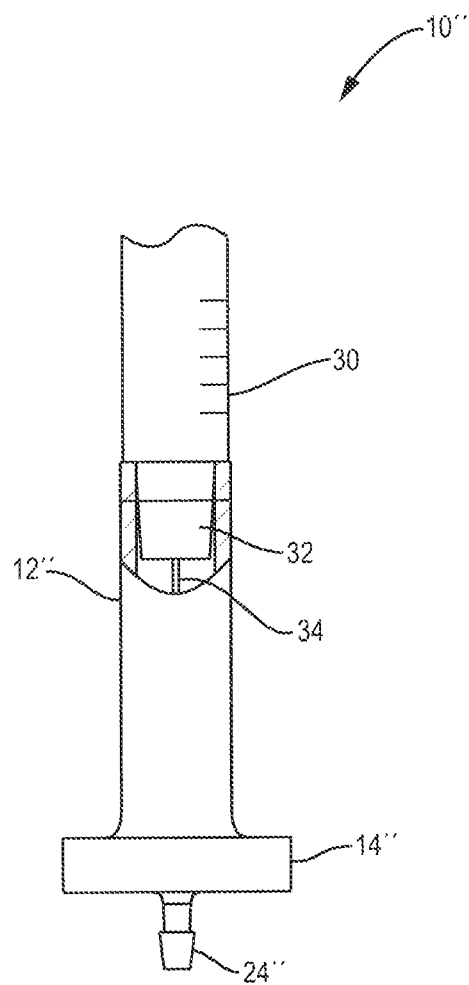
FIG. 6 is a side partial sectional view of a combination needle filter apparatus and syringe assembly according to a further embodiment of the disclosure.

In an alternative embodiment shown in FIG. 6, a needle filter apparatus shown generally as 10" includes a filter body 14" that defines a filter chamber for housing a filter. Extending from a second end of apparatus 10" is an extended neck 12" configured and dimensioned to receive a syringe and attached needle in similar fashion to the method of attachment to neck 12' of apparatus 10'. Neck 12" shares the same features of neck 12' as disclosed herein. In contrast to apparatus 10', apparatus 10" has a barb 24" extending from a first end of filter body 14" in place of slip seal post 24' configured to receive tubes and like elements useful for drawing fluids from containers and vessels accessible with an elongate tube. The method of using apparatus 10" is substantially the same as the method of use for apparatus 10' with the exception of the means used to access the fluid/solution desired for aspiration.

Figure 10:
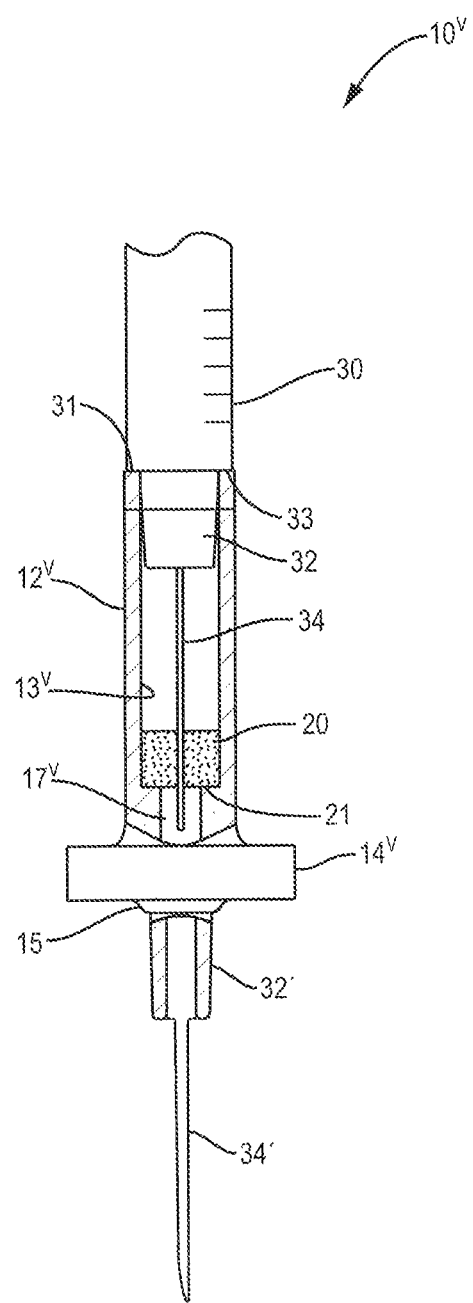
FIG. 10 is a side partial sectional view of a combination needle filter apparatus and syringe assembly according to a still further embodiment of the disclosure.

In a further alternative embodiment shewn in FIG. 10, a needle filter apparatus shown generally as 10$^V$ includes a filter body 14$^V$ that defines a filter chamber 11$^V$ for housing a filter. Extending from a second end of apparatus 10$^V$ is an extended neck 12$^V$ configured and dimensioned to receive a syringe 30 and attached needle 34 in similar fashion to the method of attachment to neck 12' of apparatus 10'. Neck 12$^V$ shares the same features of neck 12' as disclosed herein. In contrast to apparatus 10', apparatus 10$^V$ has an accessory needle 34' secured via an accessory needle hub 32' to a first end of filter body 14$^V$ in place of slip seal port 24'.

Accessory needle 34' is configured to draw fluids from containers such as vials that require the insertion of a needle into a membranous cap, or containers such as ampules that require a relatively narrow neck portion to be snapped off to access the fluid. The method of using apparatus 10$^V$ is substantially the same as the method of use for apparatus 10' with the exception of the means used to access the fluid/solution desired for aspiration. Like apparatus 10', apparatus 10$^V$ may be discarded after use. For user convenience, apparatus 10$^V$ may be provided in kit form with a corresponding syringe/needle assembly.

Figure 7:
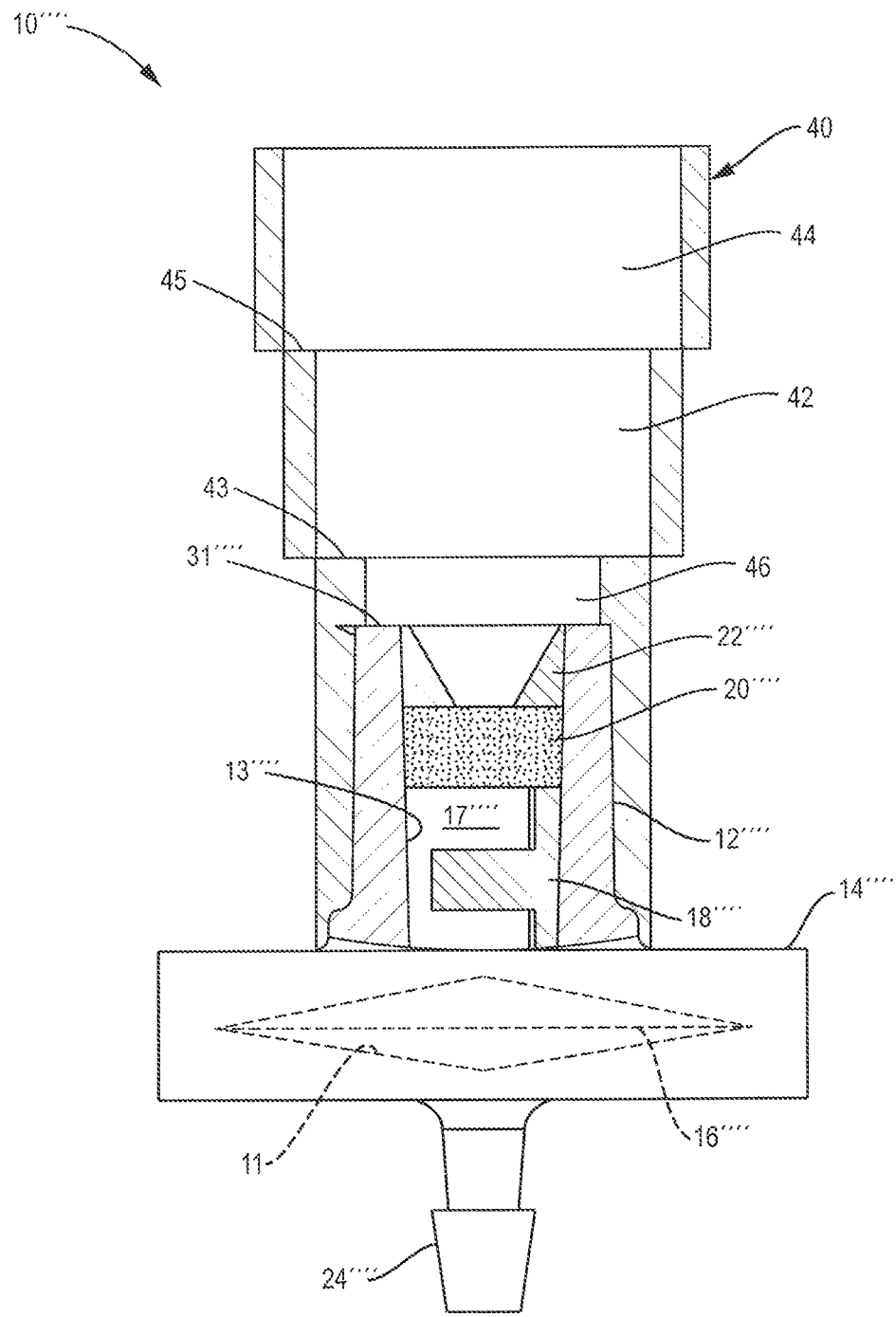
FIG. 7 is a side partial sectional view in partial phantom of a needle filter apparatus with a stepped tapered syringe receiving neck according to another embodiment of the disclosure.

Referring now to FIG. 7, in a yet further aspect of the disclosure, a needle filter apparatus shown generally as 10"" includes a stepped tapered extended neck 40 configured and dimensioned to accommodate syringes with different cross-sectional diameters and lengths. In the embodiment shown in FIG. 7, neck 40 is modular in configuration and fits superposed about truncated neck 12"". Alternatively, neck 40 may be made an integral part of the apparatus during the molding process. The combination of stepped neck 40 and truncated neck 12"" functions as a hybrid of apparatus 10 and apparatus 10' by providing additional contact surfaces for alignment of a syringe to the apparatus Apparatus 10"" has elements substantially identical to the elements of apparatus 10. A filter body 14"" has portions defining a filter chamber for housing a fitter 16"". An inlet 24"" extends from a first end of body 14"" and defines a channel in fluid communication with the filter chamber. A truncated neck 12"" extends from a second end of body 14"" and has an inner wall 13"" that defines a chamber 17"". Neck 12"" encloses a stopper 20"" in similar manner to neck 12 and may, or may not be formed with a needle stop shoulder 18"". The embodiment shown includes shoulder 18"". It should be understood that the incorporation of neck 40 eliminates the need for shoulder 18"" as explained below.

Neck 40 includes a series of consecutive annular tapered segments 42 and 44 each having a larger cross-sectional diameter than a preceding segment. The tapers are longitudinal in cross-section. The junction of the segments form annular shoulders, 43 and 45 configured and dimensioned to function as stops to limit the intrusion distance travelled by a syringe/needle assembly inserted into the apparatus. A first tapered segment 46 located the most proximal of all the segments to body 14"" may use annular surface 31"" of neck 12"" as its annular shoulder for limiting syringe insertion. As should be understood from a review of FIG. 7, the larger the syringe, the more distal the segment engaged by the syringe assembly will be from body 14"". By including additional contact surfaces for syringe engagement, alignment and control of the syringe in relation to the apparatus is improved.

As with the other embodiments and aspects of the needle filter apparatus, apparatus 10"" is intended to provide a means to filter a fluid/solution for aspiration into a syringe after which the apparatus may be discarded. The method of using apparatus 10"" is substantially identical to the methods of use for apparatuses 10 and 10' as disclosed herein.

Figure 8:
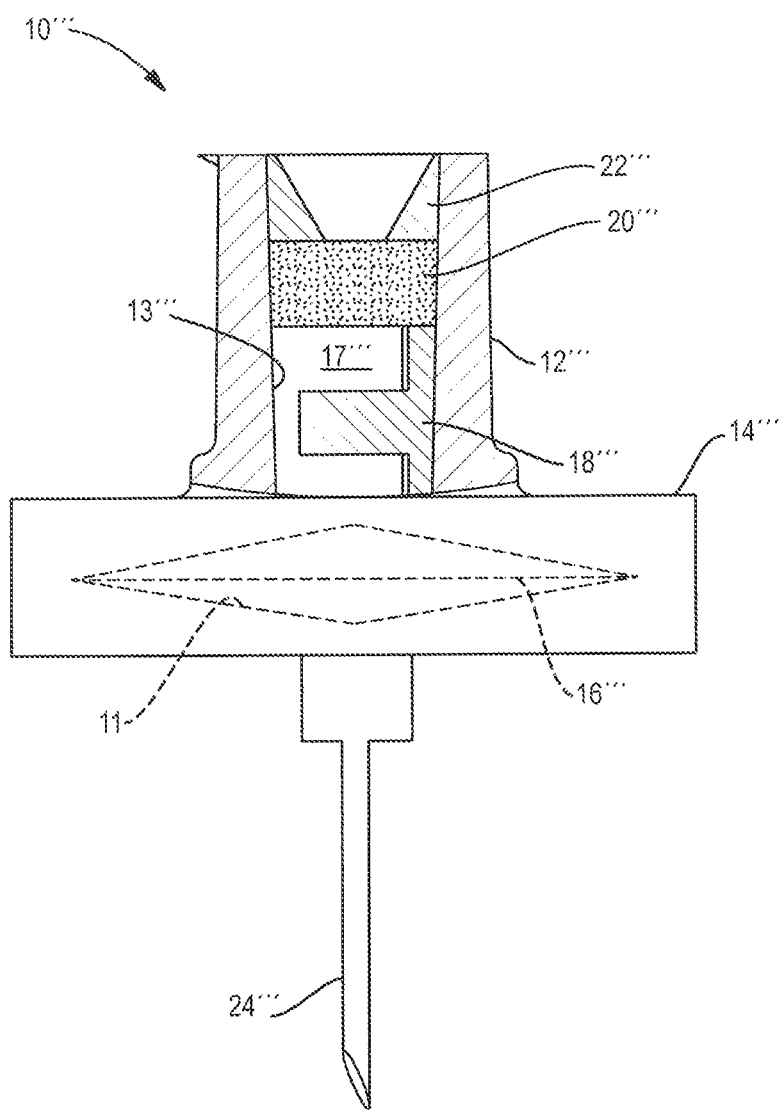
FIG. 8 is a side partial sectional view in partial phantom of a needle filter apparatus with a pre-attached needle according to a still further embodiment of the disclosure.

Referring now to FIG. 8, a yet further embodiment of the needle filter apparatus is shown generally as 10'''. This embodiment is substantially identical to needle filter apparatus 10 in construction and use. The exception is the substitution of a needle 24"" for inlet port 24. Needle 24''' is secured to filter body 14''' via hub 25 that may be structured with luer lock features, slip seal configuration features, secured via adhesive and the like. Hub 25 may also be an integral part of the apparatus incorporated in the molding process. Apparatus 10''' may also be provided with a needle cover (not shown) for apparatus needle $24'''$ for use before and after apparatus $10'''$ has been used.

This embodiment is particularly useful when the fluid/solution to be filtered is contained in a sealed ampule or like container that requires penetration of a sealing membrane or cap. Like with apparatus 10, a syringe/needle configuration is secured to apparatus $10'''$ in like manner used for apparatus 10 and the combined assembly is maneuvered to insert apparatus needle $24'''$ into the desired fluid/solution container so as to submerge the needle's tip below the fluid surface. The process for drawing out the fluid is the same as that for apparatus 10. Apparatus $10'''$ may be discarded after use.

Figure 9:
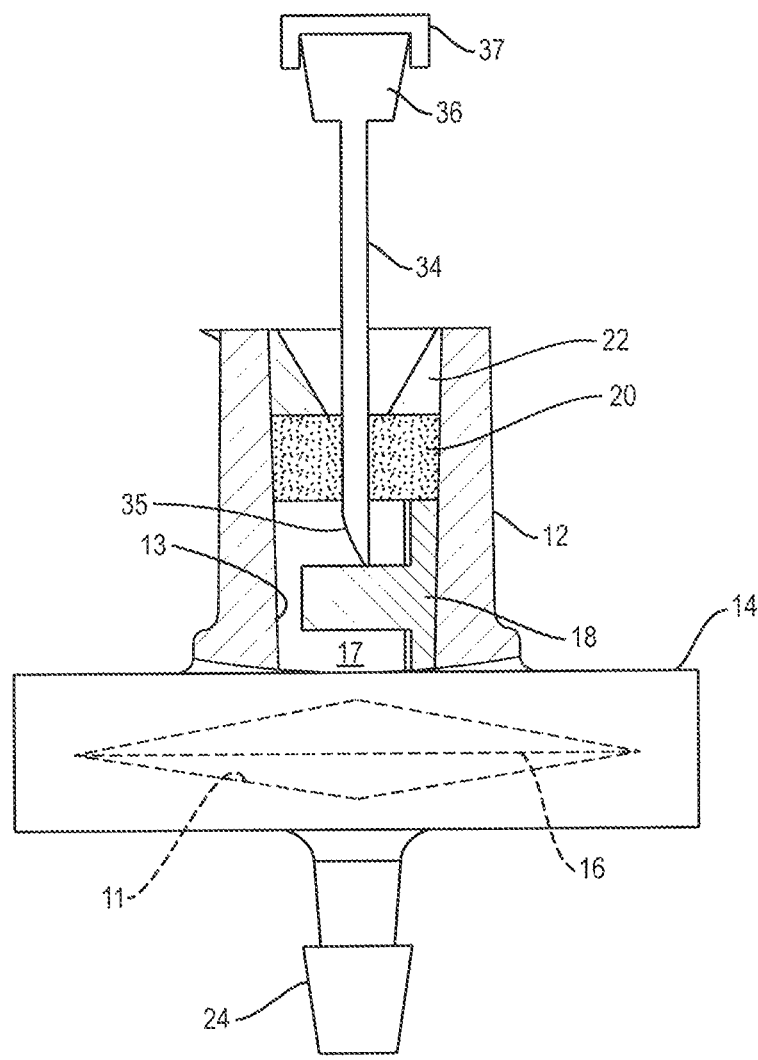
FIG. 9 is a side partial sectional view in partial phantom of a needle filter apparatus with a pre-attached syringe needle secured to the syringe-receiving neck according to an additional embodiment of the disclosure.

In a yet further aspect of the disclosure as shown in FIG. 9, a needle filter apparatus shown generally as 10 may include a pre-attached syringe needle assembly shown generally as 34. Needle 34 is secured to apparatus 10 by piercing stopper 20 with the needle and advancing the needle until needle tip 35 passes completely through stopper 20. Needle 34 may or may not be advanced until registration with shoulder 18. If pre-attached, an optional needle-hub cap 37 may be secured to a hub 36 of needle 34. The means used to secure cap 37 to hub 36 may include luer lock and slip seal configuration features as is well known in the art.

The materials used to construct shoulder 18 should have sufficient resiliency to prevent penetration of a hypodermic needle. This ensures needle tip 35 and the needle lumen remain patent throughout the aspiration and filtering process.

Figure 13:
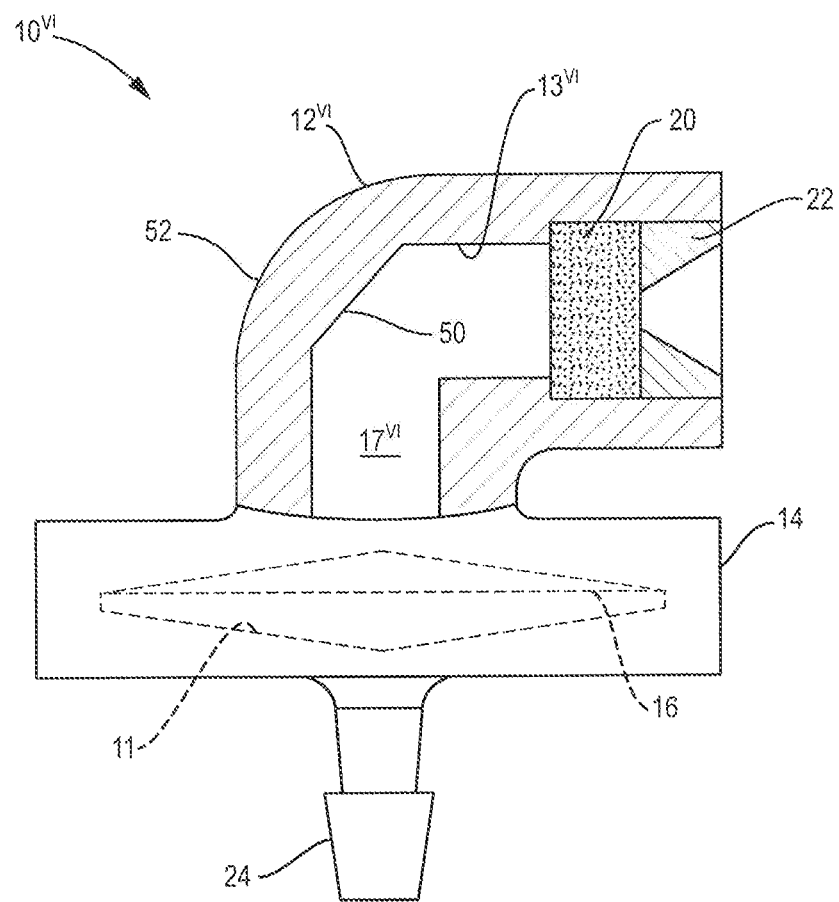
FIG. 13 is a side sectional view in partial phantom of a needle filter apparatus with an elbow neck according to an alternative embodiment of the disclosure.
Figure 14:
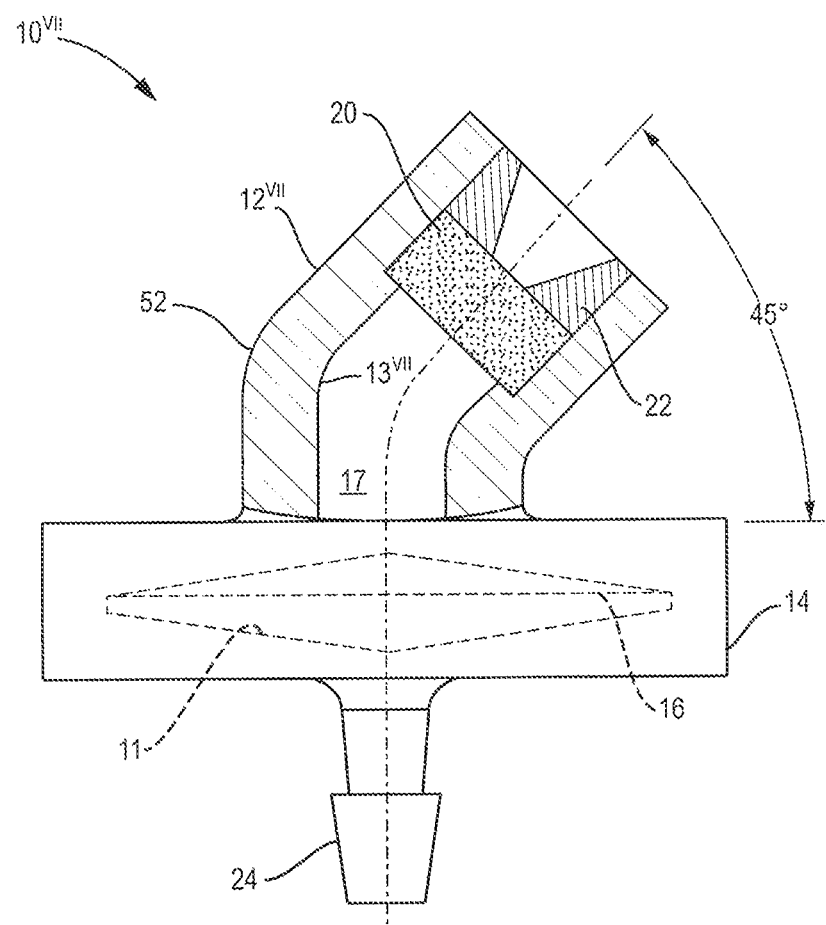
FIG. 14 is a side sectional view in partial phantom of a needle niter apparatus with an modified elbow neck according to a further alternative embodiment of the disclosure.

In a still further aspect of the disclosure shown in FIGS. 13-18, alternative embodiments of the needle filter apparatus have constructions that eliminate the need for needle stop shoulder 18. Referring now to FIG. 13, a needle filter apparatus shown generally as $10^{vi}$ includes the same features as apparatus 10 except for the exclusion of needle stop shoulder 18. In place of shoulder 18, neck $12^{vi}$ is formed with an elbow 52 to change the angle or orientation of the neck opening relative to body 14. In FIG. 13, the distal portion of the neck is offset approximately 90° from the axis perpendicular to the plane occupied by filter 16. The offset angle can be varied significantly without compromising the function of the elbow configuration. FIG. 14 shows an alternate embodiment with the distal portion of neck $12^{vii}$ offset approximately 45°.

Stopper 20 is secured in the distal portion of neck $12^{vi}$ (or neck $12^{vii}$ in FIG. 14) downstream from elbow 52. The change in angular orientation causes any syringe needle inserted into the neck and stopper 20 to register against an elbow inner wall 50 in chamber $17^{vi}$ (or $17^{vii}$ in FIG. 14). Wall 50 may be configured as a planar surface (shown), as a radiused surface that follows the general shape and contour of the elbow portion of neck $12^{vi}$, or as a non-planar surface. Regardless of the angle or orientation of insertion, any needle introduced into apparatus $10^{vi}$ (or $10^{vii}$) will not be able to reach, and therefore, not be able to penetrate filter 16 due to the geometries of the apparatus elements. Because of these geometries, the need for stop shoulder 18 is eliminated.

Figure 15:
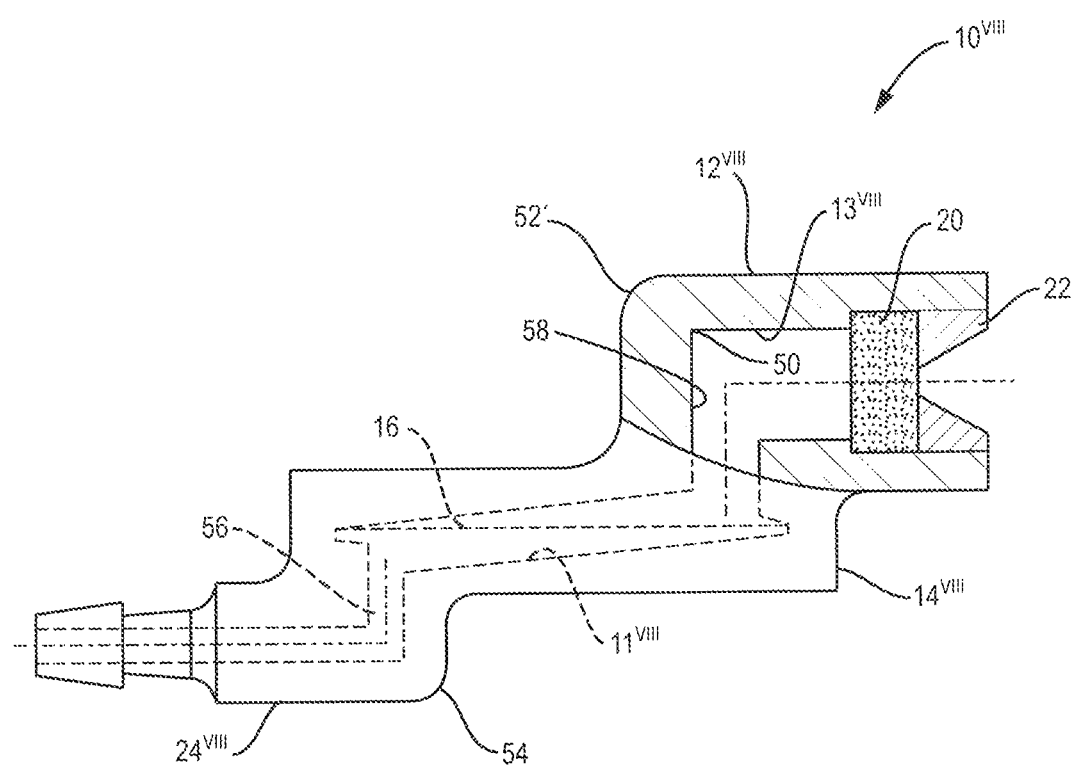
FIG. 15 is a side sectional view in partial phantom of a needle filter apparatus with an elbow neck and elbow inlet according to a still further alternative embodiment of the disclosure

Referring now to FIG. 15, a yet further aspect of the disclosure is shown with a modified neck and modified inlet. In this embodiment in which the apparatus is shown generally as $10^{viii}$, neck $12^{viii}$ originates from an end of body $14^{viii}$ rather than from an approximate center section as shown in prior embodiments. Neck $12^{viii}$ is formed with essentially the same elbow 52 disclosed in FIG. 13 except inner elbow wall 52' is configured as a substantially sharp approximately 90° corner. This configuration results in the formation of an inner neck back wall 58 positioned in direct alignment with a central axis of stopper 20. This geometric configuration causes any syringe needle inserted into the neck and stopper 20 to register against back wall 58. Regardless of the angle or orientation of insertion, any needle introduced into apparatus $10^{viii}$ will not be able to reach, and therefore, not be able to penetrate filter 16 due to the geometries of the apparatus elements.

An additional alteration of this embodiment is seen in the walls of filter chamber $11^{viii}$. To promote better flow of fluid through the chamber, the walls of chamber $11^{viii}$ are tilted relative to the plane occupied by body $14^{viii}$. This promotes the up flow of any air or gas that enters into the chamber and increases the area between filter 16 and the junctions of the chamber with inlet port $24^{viii}$ and with neck $12^{viii}$.

In similar fashion to neck $12^{viii}$, inlet port $24^{viii}$ originates from an end of body $14^{viii}$ opposite the end from which neck $12^{viii}$ originates. Like neck $12^{viii}$, inlet $24^{viii}$ is formed with an inlet elbow 54 and a corresponding channel elbow 56 in fluid communication with the entry segment of the inlet channel and the segment connected to, and in fluid communication with, chamber $11^{viii}$. In this embodiment, both the neck elbow and the inlet elbow are configured to be approximately 90°, but in opposite directions so as to create entry and exit points set approximately 180° apart, albeit with a stepped interval in the form of body $14^{viii}$. This configuration allows for the aspiration of fluids from containers or vessels requiring lateral access.

Figure 16:
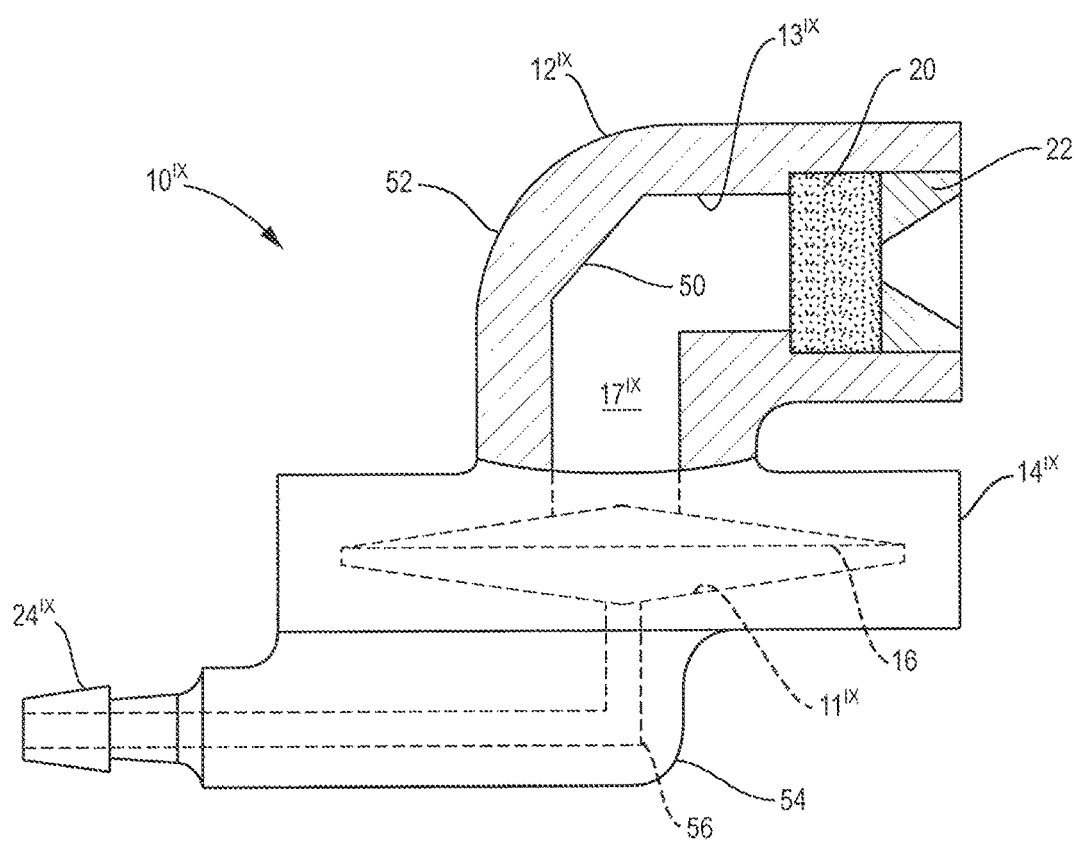
FIG. 16 is a side elevational view of a needle filter apparatus with a swivel elbow neck and a centrally oriented elbow inlet according to a yet further alternative embodiment of the disclosure.
Figure 17:
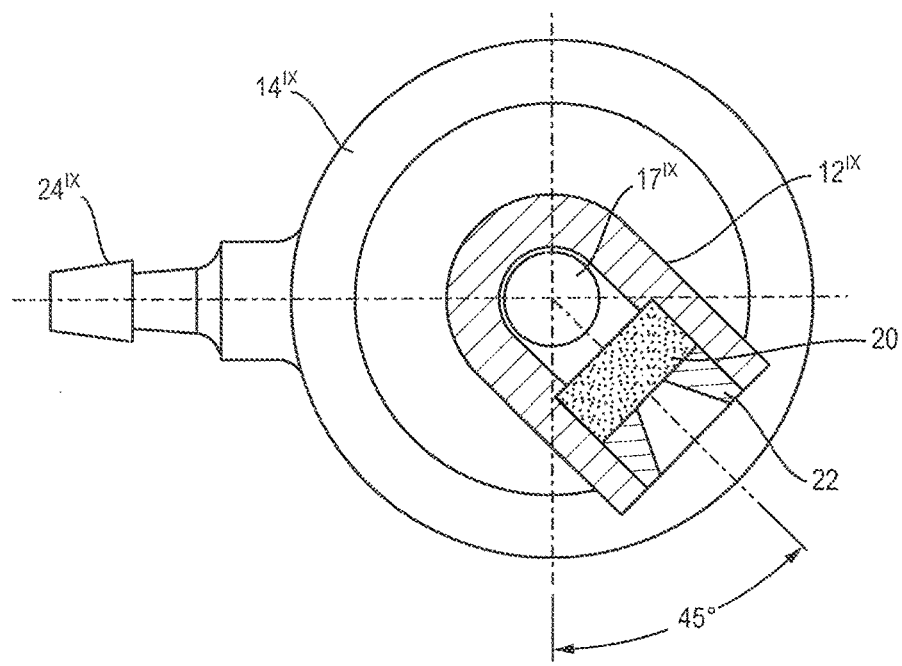
FIG. 17 is a top elevational view of the needle filter apparatus with an offset swivel elbow neck and a centrally oriented elbow inlet according to the embodiment of the disclosure shown in FIG. 16.
Figure 18:
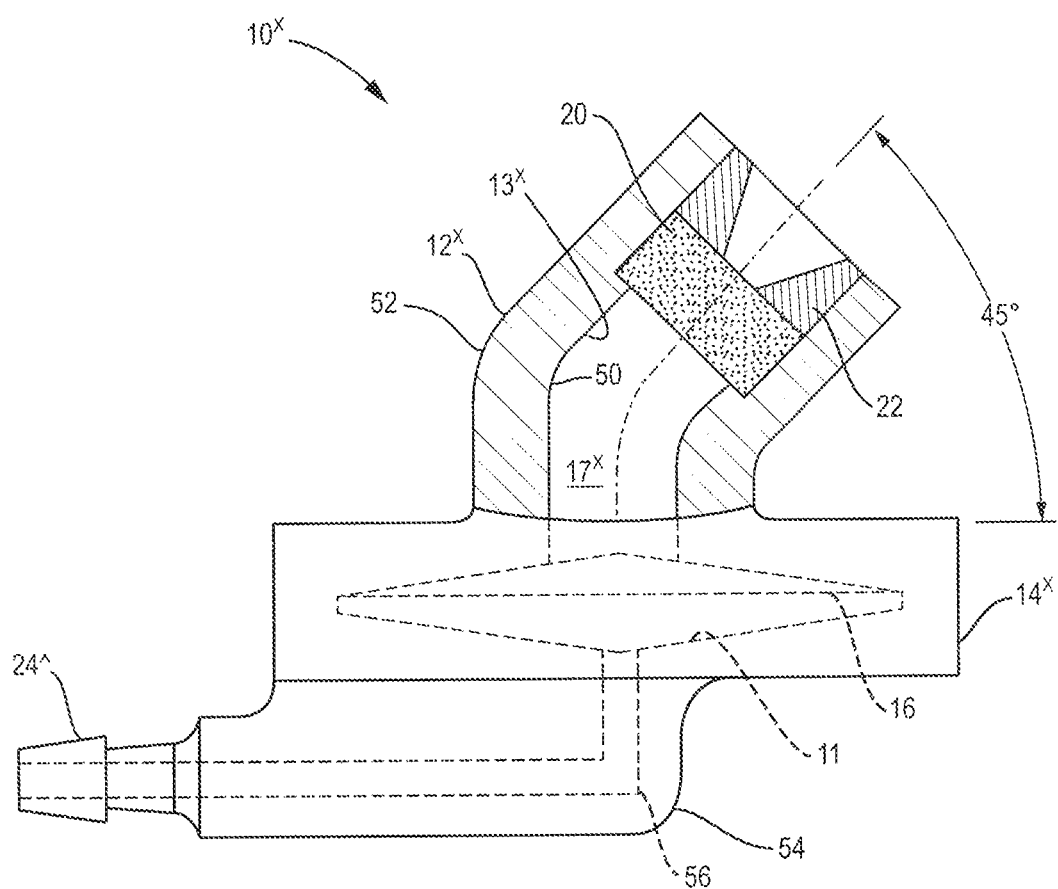
FIG. 18 is a side elevational view of a needle filter apparatus with a 45° elbow neck and centrally oriented elbow inlet according to still another embodiment of the disclosure.

Referring now to FIGS. 16 and 17, in a yet further alternative aspect of the disclosure, a needle filter apparatus shown generally as $10^{IX}$ includes a swivel elbow neck $12^{IX}$. In this embodiment, neck $12^{IX}$ originates substantially in alignment with a center of body $14^{IX}$. Body $14^{IX}$ and a proximal end of neck $12^{IX}$ are formed with annular interlocking surfaces that permit the substantially free rotation of neck $12^{IX}$ about a central axis of body $14^{IX}$. Sealing elements, e.g., o-ring, etc. are used to create a substantially air tight seal at the body/neck junction. This adds an extra degree of freedom to orient the apparatus for specific applications by swiveling neck $12^{IX}$ to a desired orientation relative to the static orientation of inlet $24^{IX}$. FIGS. 16 and 17 show the neck elbow with a 90° bend. FIG. 18 shows the same swivel elbow with a 45° bend. It should be understood the elbow angle can be modified from these illustrative angles without departing from the spirit and scope of the disclosure. In like fashion, the 90° angle of elbow 54 of inlet $24^{IX}$ can be modified in a similar manner.

Neck $12^{IX}$ (or $12^{X}$ in FIG. 18) is configured substantially the same as the neck of apparatus $10^{vi}$ shown in FIG. 13. The elbow formed in the neck replaces shoulder 18 as a registration/stop surface for a syringe needle.

Inlet port $24^{IX}$ (or $24^{X}$ in FIG. 18) is configured substantially the same as the inlet port of apparatus $10^{viii}$ shown in FIG. 15 except the point of origin is shifted to a central section of body $14^{IX}$ (or $14^{X}$ in FIG. 18). The configuration allows for the same lateral access to fluid-containing vessels.

Figure 21:
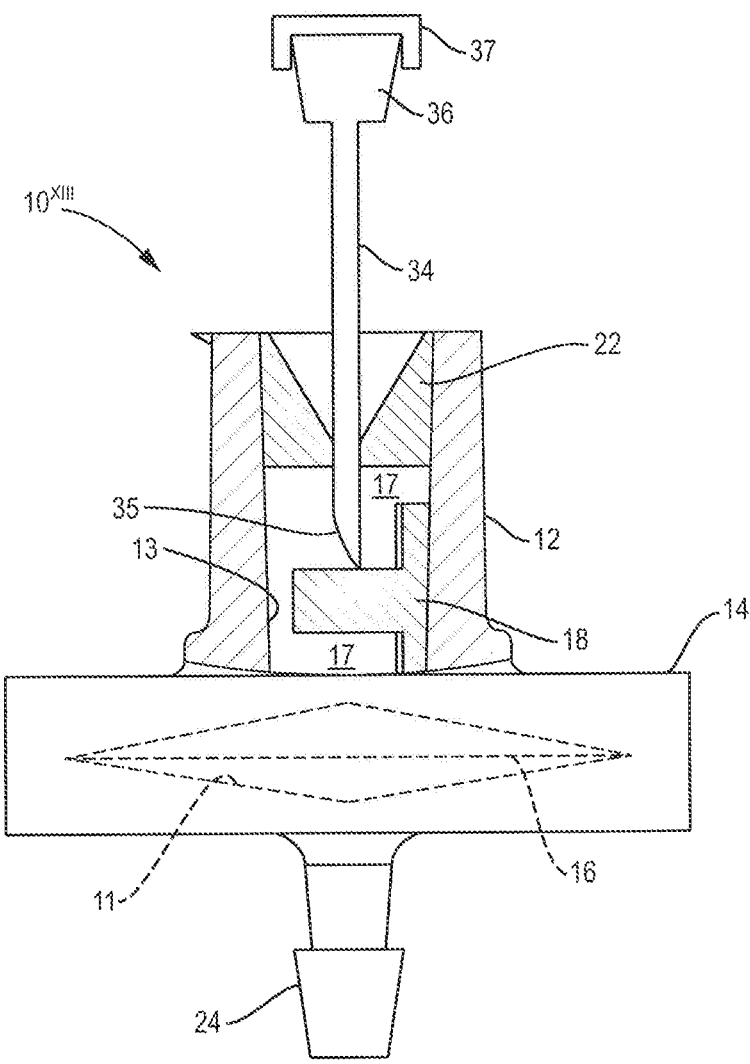
FIG. 21 is a side sectional view in partial phantom of a needle filter apparatus with a needle sealing neck according to a further embodiment of the disclosure.

In a still further aspect of the disclosure in which stopper 20 is eliminated, neck configurations permit the formation of a direct seal with either a syringe needle, a syringe hub, a syringe barrel, and/or combinations of the three. Referring now to FIG. 21, needle filter apparatus shown generally as $10^{XIII}$ is configured substantially the same as apparatus 10 with the exception that retainer ring $22^{XIII}$ is dimensioned and configured to receive syringe needle 34 so as to create a seal between the outer wall of the needle and an annular inner wall of ring $22^{XIII}$. The tight tolerance of the corresponding dimensions provides a sufficient seal to allow for the generation of a vacuum in neck chamber $17^{XIII}$ without the presence of stopper 20. Ring $22^{XIII}$ should be constructed from a material with sufficient inherent lubricity to allow for the insertion of needle 34. Alternatively, a lubricant can be used to ease needle insertion.

Referring now to FIG. 22, an alternate embodiment of the needle filter apparatus is shown generally as $10^{XIV}$ in which the cross-sectional diameter of neck inner wall $13^{XIV}$ is dimensioned to create a friction fit (press fit) with syringe hub 32. FIG. 23 shows a similar configuration in which the cross-sectional diameter of neck inner wall $13^{XV}$ is dimensioned to create a friction fit with an outer wall of syringe barrel 30. These configurations eliminate the need for stopper 20 in order to create the vacuum in neck chamber $17^{XIV}$ (or chamber $17^{XV}$ FIG. 23) necessary to effectuate fluid aspiration into the apparatus and the adjoined syringe/needle assembly.

Referring now to FIGS. 24 and 25, additional alternate embodiments of the needle filter apparatus are shown that incorporate threaded segments to secure a correspondingly threaded syringe. In FIG. 24, the apparatus shown generally as $10^{XVI}$ has a distal end of inner wall $13^{XVI}$ formed with threading to engage corresponding threading on syringe hub 32. In FIG. 25, the apparatus shown generally as $10^{XVII}$ has a distal end of inner wall $13^{XVII}$ formed with threading to engage corresponding threading on syringe barrel 30. These configurations also eliminate the need for stopper 20 in order to create the vacuum in neck chamber $17^{XVI}$ in FIG. 24 (or $17^{XVII}$ in FIG. 25) necessary to effectuate fluid aspiration into the apparatus and the adjoined syringe/needle assembly.

It should be understood the configurations disclosed to secure the syringe/needle assembly to the apparatus are illustrative in purpose and should not be considered as limiting in scope. Additional alternatives for connecting a syringe to the apparatus so as to create a seal include, but are not limited to, interference fit features such as corresponding luer lock features (male luer configuration on one, female configuration on the other), and slip seals such as o-rings. Any known means for securing a syringe to the apparatus should be considered within the scope of the disclosure.

The filters used in any of the disclosed embodiments of the needle filter apparatus may be constructed from hydrophobic, hydrophilic or hybrid combination hydrophobic/hydrophilic materials. One or multiple layers or membranes with the same or different hydrophobicity and/or hydrophilicity properties may be used to filter the desired fluid/solution. The use of both hydrophilic and hydrophobic filter media is particularly advantageous in certain applications that involve the presence of both aqueous liquids and gases. The hydrophilic media permits the passage of the fluid component through the filter while the hydrophobic media permits the passage of the gaseous component through the filter. This assures flow will not be interrupted or blocked due to the specific characteristics of the fluid/gas mixture.

Multiple layers can also be implemented with any of the disclosed apparatus embodiments to perform different tasks such as pre-filtration or other filtration process enhancements, e.g., removal by non-sieving adsorption, combined sieving and non-sieving mechanisms, ionic charges, etc. Hydrophilic and hydrophobic media and/or membrane types can be used exclusively or in combination to achieve the desired pre-filtration and/or other enhanced filtration objectives that fall within the spirit and scope of the disclosure. A pre-filter media can also be implemented at the inlet or outlet fitting to the filter. Any media type including very coarse sponge or screen pre-filter versions can be used for the purpose of pre-filtration or other enhancements of the filtration process.

Filter materials that exhibit spontaneously wettable properties are also advantageous to the disclosure. Spontaneously wettable material is particularly suitable for the filter apparatus as it allows for the substantially spontaneous wetting out of the filter material to promote and maximize fluid flow through the media.

Each filter media is constructed from fibrous material, including, but not limited to, microfibers and nanofibers of polyethylene, polypropylene, nylon, polyester, carbon, fiberglass, polypropylene sulfide (PPS), Polytetrafluoro-ethylene (Teflon® PTFE), polyvinylidene fluoride (PVDF), polyacrylonitrile (PAN), Ethylene chlorotrifluoroethylene (ECTFE), polyethylene/ultra-high molecular weight polyethylene (PE/UPE) including cellulose/diatomaceous earth or silica blends, cellulose/carbon particles or fibers, cellulose/ion exchange resins, cellulose acetate, nitrocellulose as are available from general media suppliers, as well as combinations of any of the disclosed filter media materials.

Still further filter materials may include microporous, hydrophilic or hydrophobic membranes, including, but not limited to, materials such as polyethersulfone, polysulfone, cellulose acetate, polyvinylidene fluoride (PVDF), and other fluoropolymers such as perfluoroalkoxy (PFA) and its derivatives, MFA (co-polymer of tetrafluoroethylene and perfluoromethyl vinyl ether and sold under the name Hyflon®), fluorinated ethylene propylene polymer (FEP) and the like, as well as combinations of any of the disclosed filter media materials.

The media may be constructed from a number of manufacturing processes including, but not limited to, wet-laid processes (similar to papermaking), wet casting, melt-cast, or dry processes such as air-laid, melt-blown, spun-bond, bi-directional starching, etc. as is well known in the art.

The apparatus described herein may be constructed from any injection-moldable thermal plastics, such as polypropylene, polyethylene, high-density polyethylene, nylon, perfluoroalkoxy (PFA), polyvinylchloride (PVC), acrylonitrile butadiene styrene (ABS), polyoxymethylene (POM), and the like. The materials are used in conventional injection molding processes to create the apparatuses in mold halves. The filter material is sonically welded into one half and the two halves are joined together in a final molding step using conventional molding practices well known in the art. A key consideration for material selection, particularly with respect to the needle stop, is to select a material with sufficient resiliency to prevent penetration from sharp metallic objects such as needles While the present disclosure has been described in connection with several embodiments thereof, it will be apparent to those skilled in the art that many changes and modifications may be made without departing from the true spirit and scope of the present disclosure. Accordingly it is intended by the appended claims to cover all such changes and modifications as come within the true spirit and scope of the disclosure.

What we claim as new and desire to secure by United States Letters Patent is:

1. A needle filter apparatus comprising:
    a filter housing having a first, upstream end with an inner upstream surface and a second, downstream end with an inner downstream surface, wherein the filter housing has portions defining a filter chamber;
    a filter media selected from the group consisting of hydrophilic, hydrophobic and combinations thereof, secured in the filter chamber, wherein the filter media divides the filter chamber into an upstream side and a downstream side, wherein the upstream surface in combination with the filter media forms an upstream side gap, and wherein the downstream surface in combination with the filter media forms a downstream side gap;

an extended syringe-receiving neck extending from the second end of the filter housing, wherein the neck has portions defining a neck chamber in fluid communication with the filter chamber, wherein the cross-sectional diameter of the neck is different than the cross-sectional diameter or the filter chamber, and wherein the neck has a top annular surface for registration against a syringe barrel; and, a needle-sealing stopper secured in the receiving neck.

2. The filter apparatus of claim 1 further comprising a needle stop shoulder secured to, or formed in the neck chamber between the filter housing and the stopper.

3. The filter apparatus of claim 1 further comprising a stopper retention ring secured in the extended syringe-receiving neck, wherein the ring registers against the stopper and prevents stopper migration or removal from the neck.

4. The filter apparatus of claim 1 further comprising an inlet port extending from a first end of the filter housing wherein the port has portions defining a port channel in fluid communication with the filter chamber.

5. The filter apparatus of claim 4 wherein an outer wall of the inlet port is configured as a barb or as a slip seal surface.

6. The filter apparatus of claim 4 further comprising a syringe needle secured to the inlet port.

7. A needle filter apparatus comprising:
a filter housing having a first, upstream end with an inner upstream surface and a second, downstream end with an inner downstream surface, wherein the filter housing has portions defining a filter chamber;
a filter media selected from the group consisting of hydrophilic, hydrophobic and combinations thereof, secured in the filter chamber;
a modular extended syringe-receiving neck secured to a connection hub extending from the second end of the filter housing, wherein the neck has portions defining a neck chamber in fluid communication with the filter chamber, and wherein the neck has a top annular surface for registration against a syringe barrel; and,
a needle-sealing stopper secured in the receiving neck.

8. The filter apparatus of claim 7 further comprising a needle stop shoulder secured to, or formed in, the neck chamber between the filter housing and the stopper.

9. The filter apparatus of claim 8 further comprising a stopper retention ring secured in the extended syringe-receiving neck, wherein the ring registers against the stopper and prevents stopper migration or removal from the neck.

10. The filter apparatus of claim 7 further comprising an inlet port extending from a first end of the filter housing wherein the port has portions defining a port channel in fluid communication with the filter chamber.

11. The filter apparatus of claim 10 wherein an outer wall of the inlet port is configured as a barb or as a slip seal surface.

12. The filter apparatus of claim 7 further comprising a syringe needle secured in the receiving neck.

13. The filter apparatus of claim 7 wherein the syringe-receiving neck comprises a series of connected annular tapered segments with each successive segment having a larger cross-sectional diameter than a preceding segment, wherein the preceding segment is located more proximal to the filter housing than the successive segment.

14. The filter apparatus of claim 7 wherein the syringe-receiving neck comprises a first tapered segment located proximal to the filter housing and a second tapered segment connected to the first tapered segment, distal from the filter housing wherein the cross-sectional diameter of the first tapered segment is smaller than the cross-sectional diameter of the second tapered segment.

15. A needle filter apparatus comprising:
a filter housing having a first, upstream end with an inner upstream surface and a second, downstream end with an inner downstream surface, wherein the filter housing has portions defining a filter chamber;
a filter media selected from the group consisting of hydrophilic, hydrophobic and combinations thereof, secured in the filter chamber, wherein the filter media divides the filter chamber into an upstream side and a downstream side, wherein the upstream surface in combination with the filter media forms an upstream side gap, and wherein the downstream surface in combination with the filter media forms a downstream side gap;
an extended syringe-receiving neck extending from the second end of the filter housing, wherein the neck has portions defining a neck chamber in fluid communication with the filter chamber, wherein the cross-sectional diameter of the neck is different than the cross-sectional diameter of the filter chamber, and wherein the neck has a distal neck end set at an angle to a portion of the neck proximal the filter housing; and,
a needle-sealing stopper secured in the distal neck end.

16. The needle filter apparatus of claim 15 wherein the filter housing and the portion of the neck proximal to the filter housing are formed with annular interlocking surfaces to permit the substantially free rotation of the neck about a central axis of the filter housing.

17. The needle filter apparatus of claim 16 further comprising a sealing element between the annular interlocking surfaces of the filter housing and the portion of the neck proximal to the filter housing.

18. The needle filter apparatus of claim 17 wherein a distal end of the neck is set at an angle to the portion of the neck proximal the filter housing.

19. The needle filter apparatus of claim 16 wherein a distal end of the neck is set at a 90° angle to the portion of the neck proximal the filter housing.

20. The needle filter apparatus of claim 16 wherein a distal end of the neck is set at a 45° angle to the portion of the neck proximal the filter housing.

* * * * *